US011413385B2

(12) United States Patent
Childers

(10) Patent No.: US 11,413,385 B2
(45) Date of Patent: *Aug. 16, 2022

(54) DIALYSIS MACHINE WITH FLUID PUMPING CASSETTE

(71) Applicants: BAXTER INTERNATIONAL INC., Deerfield, IL (US); BAXTER HEALTHCARE SA, Glattpark (CH)

(72) Inventor: Robert W. Childers, New Port Richey, FL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 901 days.

This patent is subject to a terminal disclaimer.

(21) Appl. No.: 16/173,665

(22) Filed: Oct. 29, 2018

(65) Prior Publication Data

US 2019/0060544 A1    Feb. 28, 2019

Related U.S. Application Data

(63) Continuation of application No. 14/553,104, filed on Nov. 25, 2014, now Pat. No. 10,117,986, which is a
(Continued)

(51) Int. Cl.
*A61M 1/28* (2006.01)
*A61M 1/36* (2006.01)
(Continued)

(52) U.S. Cl.
CPC .............. *A61M 1/284* (2014.02); *A61M 1/28* (2013.01); *A61M 1/281* (2014.02); *A61M 1/288* (2014.02);
(Continued)

(58) Field of Classification Search
CPC ...... A61M 1/284; A61M 1/281; A61M 1/288; A61M 1/3644; A61M 1/3652; A61M 1/28;
(Continued)

(56) References Cited

U.S. PATENT DOCUMENTS

| 6,814,547 | B2 * | 11/2004 | Childers | ............... A61M 1/288 417/53 |
| 8,070,709 | B2 * | 12/2011 | Childers | ................. G01M 3/04 604/9 |
| 8,900,174 | B2 * | 12/2014 | Childers | ............... A61M 1/281 604/6.11 |

* cited by examiner

*Primary Examiner* — Philip R Wiest
(74) *Attorney, Agent, or Firm* — K&L Gates LLP

(57) ABSTRACT

A dialysis system is disclosed. The example dialysis system includes a housing, a pump actuator housed by the housing, a fluid pumping cassette coupled operably to the housing and including a flexible membrane covering a pump chamber, and a mechanically actuated piston head provided by the pump actuator and positioned to extend towards and away from the fluid pumping cassette. The fluid pumping cassette is positioned such that the flexible membrane of the fluid pumping cassette faces the piston head so that the piston head can push the flexible membrane into the pump chamber of the fluid pumping cassette to expel a fluid from the pump chamber. The example dialysis system also includes a controller programmed to perform a leak test by monitoring a sensed position of the mechanically actuated piston head while the mechanically actuated piston head applies a force to the flexible membrane of the fluid pumping cassette.

10 Claims, 17 Drawing Sheets

Related U.S. Application Data continuation of application No. 13/373,909, filed on Dec. 5, 2011, now Pat. No. 8,900,174, which is a continuation of application No. 12/506,738, filed on Jul. 21, 2009, now Pat. No. 8,070,709, which is a continuation of application No. 10/975,733, filed on Oct. 27, 2004, now Pat. No. 7,575,564.

(60) Provisional application No. 60/515,815, filed on Oct. 28, 2003.

(51) Int. Cl.
  *G01L 7/00* (2006.01)
  *G01M 3/04* (2006.01)
  *A61B 5/02* (2006.01)

(52) U.S. Cl.
  CPC ........ *A61M 1/3621* (2013.01); *A61M 1/3639* (2013.01); *A61M 1/3641* (2014.02); *A61M 1/3643* (2013.01); *A61M 1/3644* (2014.02); *A61M 1/3652* (2014.02); *G01L 7/00* (2013.01); *G01M 3/04* (2013.01); *A61B 5/02042* (2013.01); *A61M 2205/122* (2013.01); *A61M 2205/128* (2013.01); *A61M 2205/70* (2013.01)

(58) Field of Classification Search
  CPC .............. A61M 1/3621; A61M 1/3639; A61M 1/3643; A61M 2205/122; A61M 2205/128; A61M 2205/70; G01L 7/00; G01M 3/04
  See application file for complete search history.

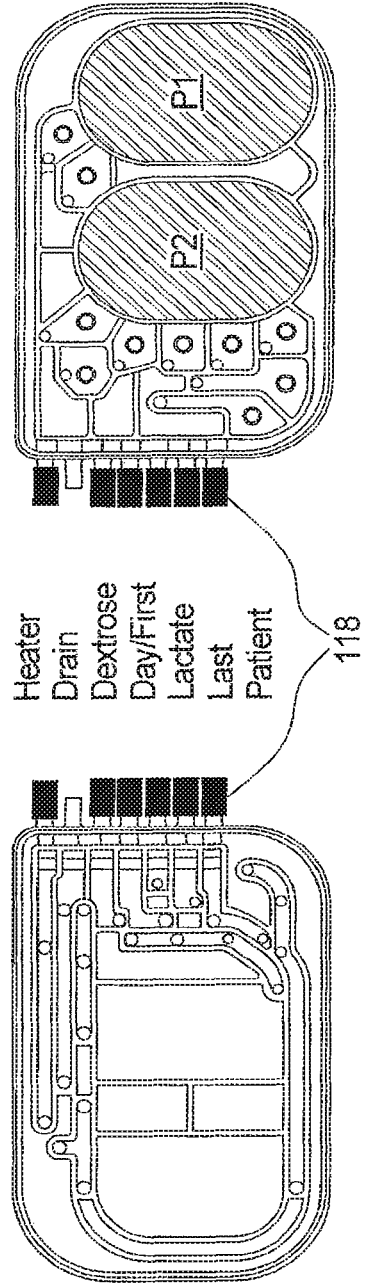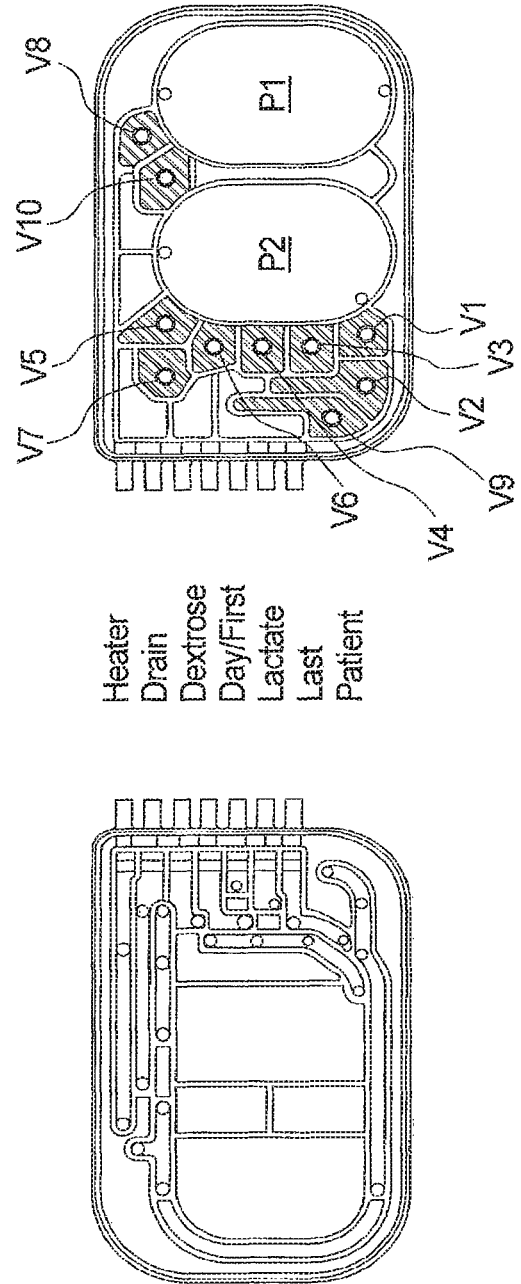

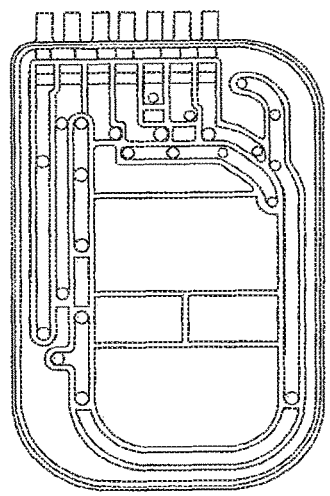
FIG. 3
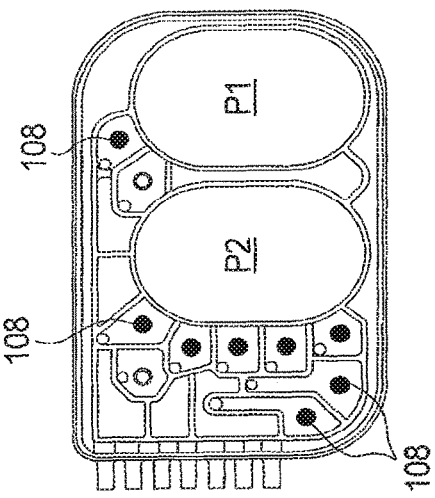
Heater
Drain
Dextrose
Day/First
Lactate
Last
Patient
Prior art test, Step 3: Positive pressure test of all but two valve centers shown darkened
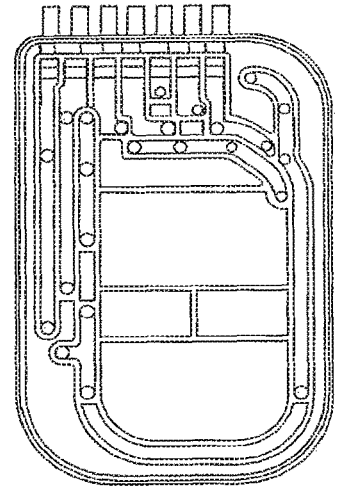
FIG. 4
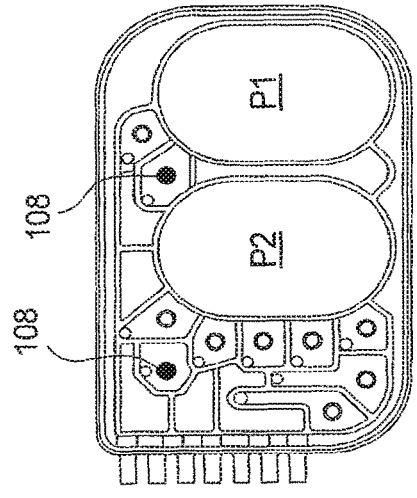
Heater
Drain
Dextrose
Day/First
Lactate
Last
Patient
Prior art test, Step 4: Positive pressure decay test of remaining two valve centers shown darkened

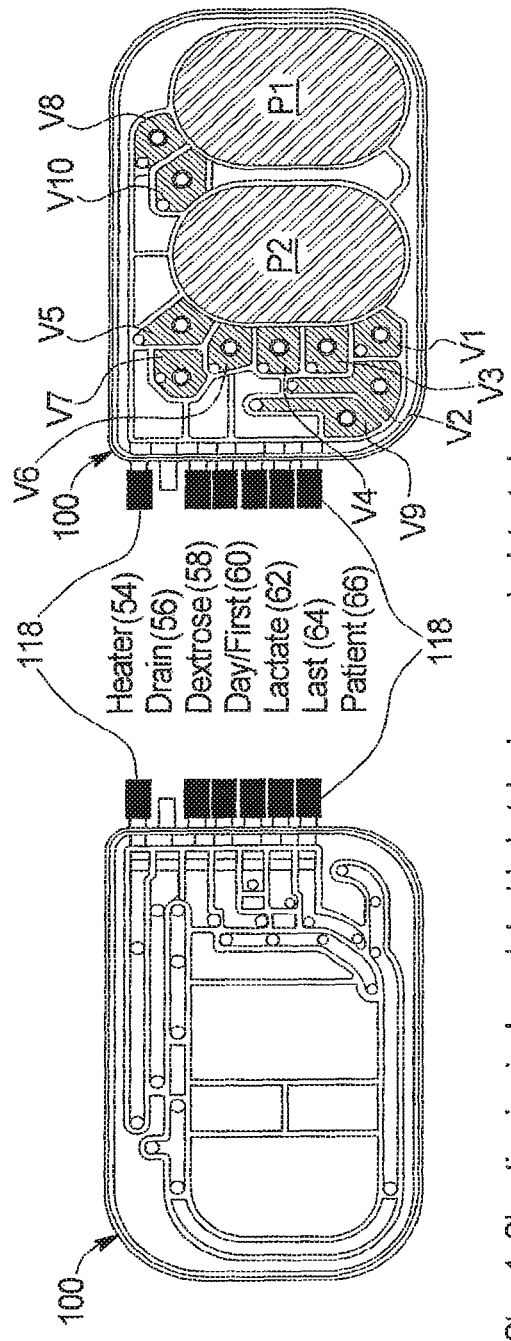

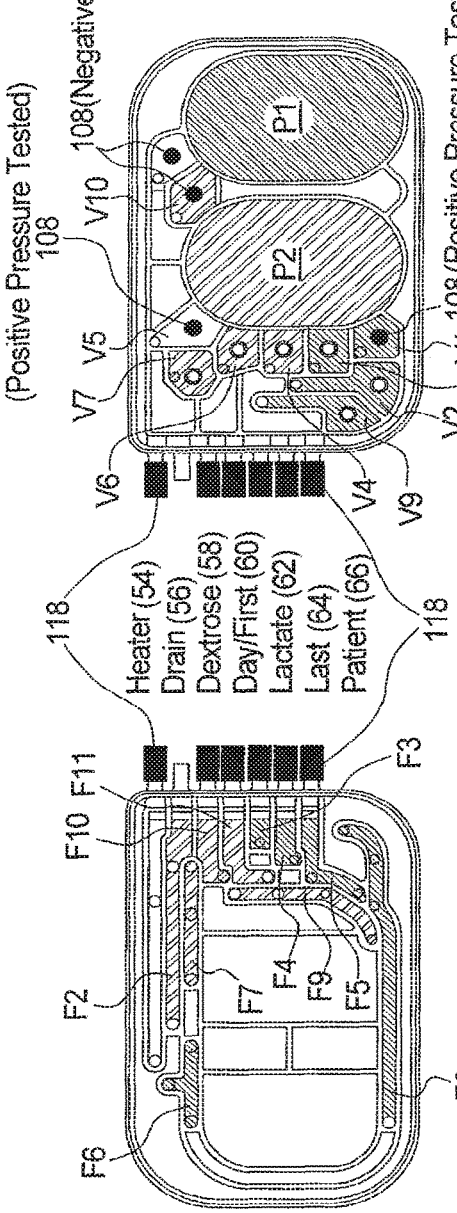

FIG. 11

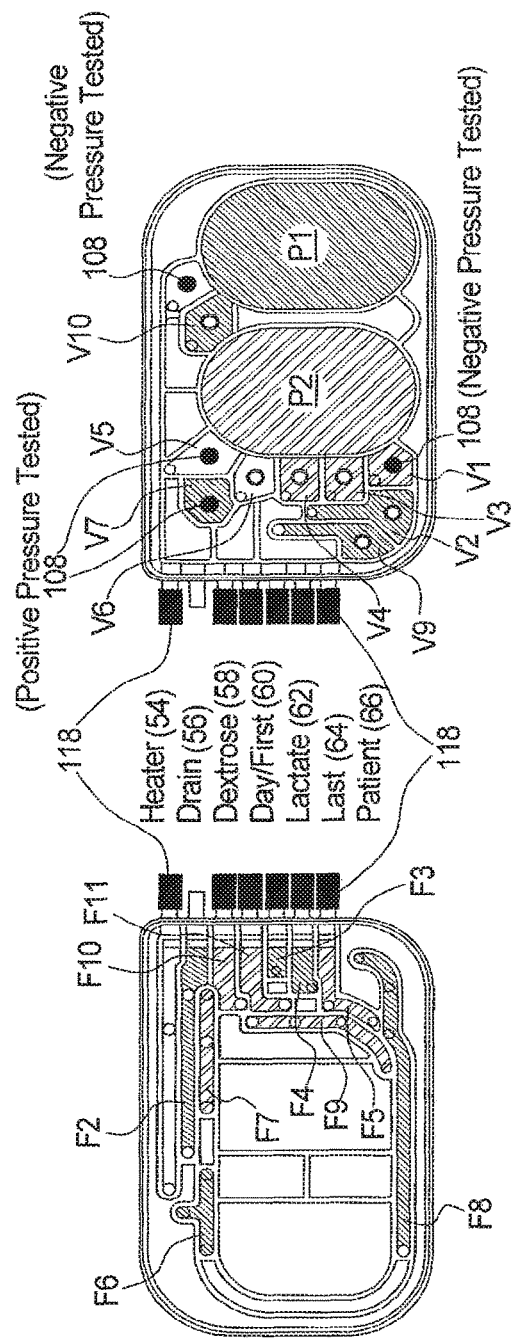

FIG. 12

Step 2: Single hatched areas and ports 108 so marked and darkened are evacuated, and double hatched areas and ports 108 so marked and darkened are pressurized and tested for leaks.

Step 3: Single hatched area and ports 108 so marked and darkened are evacuated, and double hatched areas and ports 108 so marked and darkened are pressurized and then both checked simultaneously for leaks.

Step 4: Single hatched areas and ports 108 so marked and darkened are evacuated, and double hatched areas and ports 108 so marked and darkened are pressurized and then both checked simultaneously for leaks.

Step 5: Single hatched areas and ports 108 so marked and darkened are evacuated to check for leaks, double hatched areas and ports 108 so marked and darkened are pressurized and checked for leaks.

Step 6: Double hatched areas and ports 108 so marked and darkened are pressurized and checked for leaks.

DIALYSIS MACHINE WITH FLUID PUMPING CASSETTE

PRIORITY CLAIM

This application claims priority to and the benefit of U.S. patent application Ser. No. 14/553,104, filed Nov. 25, 2014, now U.S. Pat. No. 10,117,986, entitled, "Peritoneal Dialysis Machine", which is a continuation of U.S. patent application Ser. No. 13/373,909, filed Dec. 5, 2011, now U.S. Pat. No. 8,900,174, entitled, "Peritoneal Dialysis Machine", which is a continuation of U.S. patent application Ser. No. 12/506, 738, filed Jul. 21, 2009, now U.S. Pat. No. 8,070,709 entitled, "Peritoneal Dialysis Machine", which is a continuation application of U.S. patent application Ser. No. 10/975, 733, filed Oct. 27, 2004, now U.S. Pat. No. 7,575,564 entitled, "Priming, Integrity and Head Height Methods and Apparatuses For Medical Fluid Systems", which claims priority to and the benefit of U.S. Provisional Patent Application No. 60/515,815, filed Oct. 28, 2003, entitled, "Improved Priming, Integrity and Head Height Methods and Apparatuses for Medical Fluid Systems", the entire contents of each of which are hereby incorporated by reference and relied upon.

BACKGROUND

The present invention relates generally to medical fluid systems and more particularly to the testing and priming of such systems.

It is known in peritoneal dialysis systems to perform integrity tests that attempt to verify that the numerous fluid valves in a disposable cassette do not leak, that leaks do not occur between multiple pump chambers in the cassette, that leaks do not occur across fluid pathways, and that an isolation occluder, which is intended to stop liquid flow in fluid lines connected to the cassette in the event of a system malfunction, is performing that procedure properly. In one known wet leak test described in U.S. Pat. No. 5,350,357, a disposable cassette is loaded into a peritoneal dialysis cycler and the solution bags are connected. The test consists of the following steps:

(i) a negative pressure decay test of the fluid valve diaphragms is performed;

(ii) a positive pressure decay test of the fluid valve diaphragms is performed;

(iii) a positive pressure decay test is performed on the first pump chamber, while a negative pressure decay test is performed on the second pump chamber;

(iv) a negative pressure decay test is performed on the first pump chamber, while a positive pressure decay test is performed on the second pump chamber; after which (v) both pump chambers are filled with a measured volume of fluid, all fluid valves are opened and the occluder is closed, positive pressure is applied to both pump chambers for a period of time, after which the volume of fluid in each pump chamber is measured again to determine if any fluid has leaked across the occluder.

As indicated, the above testing procedure is performed after solution bags are connected to the peritoneal dialysis system. If integrity of the cassette or tubing is faulty, the sterility of the solution bags becomes compromised. In such a case, both the disposable cassette and solution bags have to be discarded. Additionally, it is possible that liquid from the solution bags can be sucked into the machine's pneumatic system, causing the pneumatic system of the machine to malfunction.

Wet tests are also susceptible to false triggers. In particular, cold solution used in the test causes many false disposable integrity test alarms each year because the tests fail when an occluder, which is supposed to clamp off all fluid lines, does not properly crimp or seal the tubing lines. When the solution is cold, it cools the set tubing to a lower temperature than the tubing would be if placed only in room air. Colder tubing is harder to occlude, allowing fluid in some cases to leak past the occluder and cause the test to fail. Once a dialysis therapy starts, the fluid passing through the tubing is warmed to about 37° C., enabling the occluder to perform satisfactorily.

It is therefore desirable to have an integrity test that is performed before the solution bags are attached to the therapy machine and to eliminate the use of cold solution to prevent false triggers.

A "dry" test is described briefly in U.S. Pat. No. 6,302, 653. The description is based in part upon the "dry test" implemented in the Baxter HomeChoice® cycler in December of 1998. The actual test implemented in the HomeChoice® cycler consists of four steps, the first of which occurs before the solution bags are connected. The next three steps require the solution bags to be connected but do not require fluid to be pulled from the bags into the machine. FIGS. 1 to 4 illustrate the areas of a fluid cassette tested by the individual steps of the known "dry" test. While the above "dry" test eliminates the problem of fluid potentially leaking into the pneumatics of the machine, the test does not prevent the sterility of the bags from being compromised potentially upon a leak and thus from being discarded if the integrity of the disposable cassette is compromised.

Moreover, dry testing with air is believed to be more sensitive than the wet test, which uses dialysis fluid. It is therefore also desirable to have an integrity test that uses air for sensitivity reasons as well as for the reasons stated above.

While integrity testing poses one problem to manufacturers of medical fluid machines, another common problem is the priming of the fluid system within those machines. In many instances, air must be purged from one or more tubes for safety purposes. For example, in the realm of dialysis, it is imperative to purge air from the system, so that the patient's peritoneum or veins and arteries receive dialysis fluid that is free of air. Consequently, automated dialysis machines have been provided heretofore with priming systems. In peritoneal dialysis, the object of priming is to push fluid to the very end of the line, where the patient connector that connects to the patient's transfer set is located, while not priming fluid past the connector, allowing fluid to spill out of the system.

Typically, dialysis machines have used gravity to prime. Known gravity primed systems have a number of drawbacks. First, some priming systems are designed for specifically sized bags. If other sized bags are used, the priming system does not work properly. Second, it happens in many systems that at the beginning of priming, a mixture of air and fluid can be present in the patient line near its proximal end close to a disposable cartridge or cassette. Fluid sometimes collects in the cassette due to the installation and/or integrity testing of same. Such fluid collection can cause air gaps between that fluid and the incoming priming solution. The air gaps can impede and sometimes prevent gravity priming. Indeed, many procedural guides include a step of tapping a portion of the patient line when the line does not appear to be priming properly. That tapping is meant to dislodge any air bubbles that are trapped in the fluid line.

A third problem that occurs relatively often in priming is that the patient forgets to remove the clamp on the patient line prior to priming that line. That clamped line will not allow the line to prime properly. An alarm is needed to inform the patient specifically that the patient needs to remove the clamp from the patient line before proceeding with the remainder of therapy. Fourth, if vented tip protectors are provided at the end of the patient line, the vented tip protectors may not vent properly and impede priming. An alarm is again needed to inform the patient that the line has not primed properly. Fifth, cost is always a factor. Besides providing a priming apparatus and method that overcomes the above problems, it is also desirable to use existing components to perform the priming, if possible, to avoid having to add additional components and additional costs.

Another concern for medical fluid systems and in particular automated peritoneal dialysis ("APD") systems is ensuring that solution bags are placed at a height relative to the machine that is suitable for the machine to operate within designated parameters. The height of solution bags, such as dialysate bags, lactate bags and/or dextrose bags, needs to be monitored to ensure that the proper amount of fluid will be pumped to the patient during therapy and that the correct amount and proportion of additives are infused. Two patents discussing bag position determination are U.S. Pat. Nos. 6,497,676 and 6,503,062.

SUMMARY

The present invention in one primary embodiment performs an integrity test on both the cassette sheeting and the molded cassette features of a disposable cassette. The methodology of the invention is applicable to many cassette based pumping and liquid distribution systems and is particularly suited for dialysis treatment, such as automated peritoneal dialysis. The steps of the integrity test are performed almost exclusively before solution bags, such as peritoneal dialysis solution bags, are connected to a dialysis therapy machine, such as a peritoneal dialysis machine. Such a test is advantageous because if an integrity problem arises, the patient only has to discard the disposable cassette and associated tubing, not the solution. Also, because fluid is not connected to the machine to perform the test, there is no opportunity for fluid, due to a leak, to be sucked into the machine's pneumatics, potentially causing malfunction.

The dry testing of the present invention is performed with all fluid lines capped except for the drain line, which is covered with a tip protector and/or membrane that allows air but not liquid to escape. Because the lines remain capped, they are not connected to the solution bags. Consequently, no solution bags become contaminated if the cassette has a leak.

The testing steps are able to be performed with capped lines for a number of reasons. In some steps, the tip protectors, or caps, connected to all lines except the drain line are left in place because the cassette sheeting and fluid pathways are tested with valves in the open position rather than the closed position. When the valves are open, all of the fluid channels in the cassette are in direct communication with both pump chambers and the drain line, which has a bacteria retentive tip protector that allows air to pass through it. Air from a failed test can therefore pass through the drain line from cassette, changing the pressure in the system so that a leak can be detected.

In other test steps, the tip protectors can be left in place because one part of the system is pressurized, while the other is evacuated. Air leaking from the positively pressurized part of the cassette leaks to the evacuated part and is readily detectable as is air escaping from or leaking into the cassette. Further, because air flows more readily than does water or solution through a leak, the air test is more expedient and sensitive than a fluid based test, increasing accuracy and repeatability and decreasing test time.

The present invention in another primary embodiment provides an apparatus and method for priming a medical fluid delivery system. The priming method and apparatus is described herein for an automated peritoneal dialysis machine, however, the test is applicable to any fluid delivery system, which requires the purging of air for safety or operational reasons. The method and apparatus operates with a system having a fluid container or fluid bag, at least one fluid pump and at least one tubing line, such as a patient line extending from that fluid pump. In a first step of the priming method, valves surrounding the fluid pump are configured so that fluid flows via gravity or via the pump into the pump chamber and fills such pump chamber but does not exit the chamber. In a second step, the valves are switched so that the fluid in the supply bag is no longer able to fill the pump chambers, and so that the pump chambers can be pressurized and thereby pump the fluid from the pump chambers downstream and partially into the patient line. The machine processor is configured to expect a pressure drop in the pump chamber when the pump chamber expels fluid therefrom. If such pressure drop is not seen, the patient has likely forgotten to remove the clamp in the patient line and an error message is generated. In a final step, the valves surrounding the pump are opened so that fluid from the container or bag can continue to flow through and prime the patient line until fluid reaches the end of the patient line, which is positioned at the same elevational height as the top of the fluid in the fluid container.

As indicated above, if the patient line is inadvertently clamped during priming, the pressure in the pump chamber during the pushing step would not fall to an expected level, prompting a suitable alarm. Further, the initial pushing of fluid through the proximal part of the patient line, nearer to the cassette, in many instances will overcome the resistance to fluid flow caused by air trapped in that portion of the line, and allow priming to thereafter take place in a proper manner.

Another primary aspect of the present invention is an apparatus and method for determining the vertical position or head height of one or more solution bags as well as a drain bag. The method and apparatus use atmospheric pressure to establish a zero position relative to the therapy machine, such as an APD machine. The bag height determination can determine whether a solution bag is in the proper position to achieve a desired pumped flowrate, whether the solution bag is properly located on a heater plate, whether the relative position between two or more bags is proper, whether the drain bag is located in a proper position or whether one or more of the bags is empty, etc.

It is therefore an advantage of the present invention to provide an integrity test that consumes less time than previous practices.

It is another advantage of the present invention to provide an integrity test that is more effective at detecting leaks than previous practices.

It is a further advantage of the present invention to provide an integrity test that is more convenient for the patient if a leak is detected.

It is another advantage of the present invention to provide an integrity test that minimizes the supplies that must be discarded if a leak is detected.

It is yet another advantage of the present invention to provide an integrity test that is immune to failure of other machine components, such as a flow line occluder.

It is still another advantage of the present invention to provide an integrity test that does not require warm solution.

It is still a further advantage of the present invention to provide an integrity test from which it is possible for a user to distinguish between a failure of the disposable set and a leak in the pneumatic system of the machine or cycler.

Moreover, it is an advantage of the present invention to eliminate false triggering due to cold solution used in integrity testing.

Still further, it is an advantage of the present invention to provide a priming method and apparatus that operates to automatically dislodge air pockets located initially in the priming line, which would otherwise tend to slow or completely stop priming.

Yet another advantage of the present invention is to provide a priming method and apparatus that detects when the patient or operator has inadvertently left a clamp on the priming line, so that the therapy machine can generate a suitable alarm.

Further still, an advantage of the present invention is to be able to determine the elevational location and head height of one or more solution and drain bags.

Additional features and advantages of the present invention are described in, and will be apparent from, the following Detailed Description of the Invention and the figures.

BRIEF DESCRIPTION OF THE FIGURES

FIGS. 1 to 4 are opposite views of a cassette showing different areas of the cassette that are integrity tested during a known integrity test.

FIGS. 10 to 15 are elevation views of opposite sides of the cassette shown in FIG. 5 illustrating the different components or areas of the cassette that are integrity tested in the various steps of one embodiment of the integrity test of the present invention.

DETAILED DESCRIPTION

One primary aspect of the present invention is an improved leak detection system for any type of cassette-based medical fluid therapy that exerts mechanical or pneumatic positive or negative pressure on a disposable fluid cassette. Another primary aspect of the present invention is an improved priming technique for a medical fluid therapy machine, such as an automated peritoneal dialysis ("APD") system. While APD is one preferred use for the present invention, any cassette-based medical fluid system or system using a sterile, disposable fluid cartridge can employ the apparatuses and methods of the present invention. A further primary aspect of the present invention is to provide an apparatus and method for determining the head weight of the solution.

Improved Cassette-Based Leak Test

The following method is a "dry" method, which is more sensitive to leaks and other defects when compared to fluid based integrity testing. The method also eliminates some problems associated with older tests, such as having to discard solution bags or potentially harming the mechanical components of the machine upon a leak.

Figure 5:
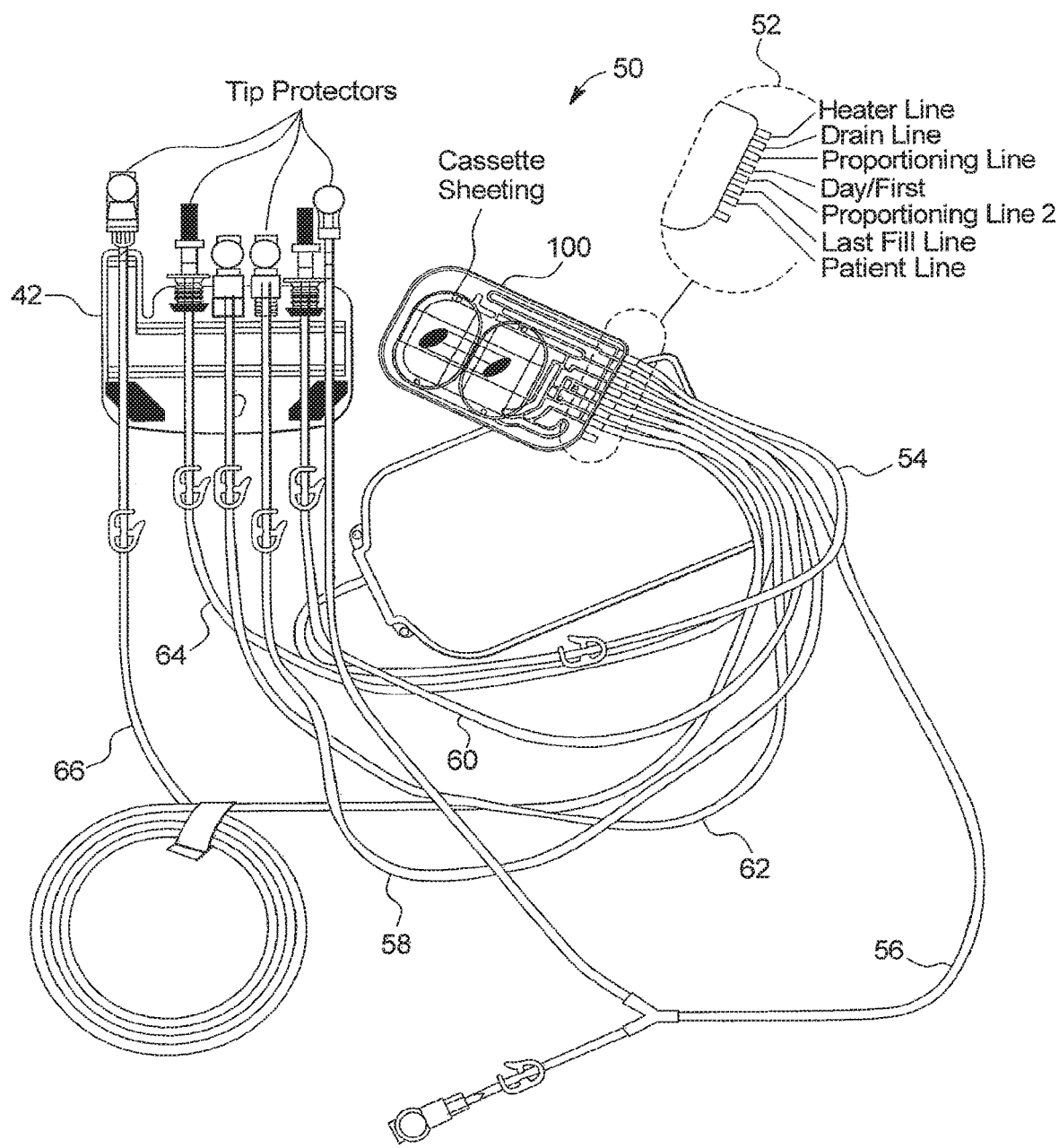
FIG. 5 is a plan view of one embodiment of a disposable set operable with the integrity test of the present invention.
Figure 6:
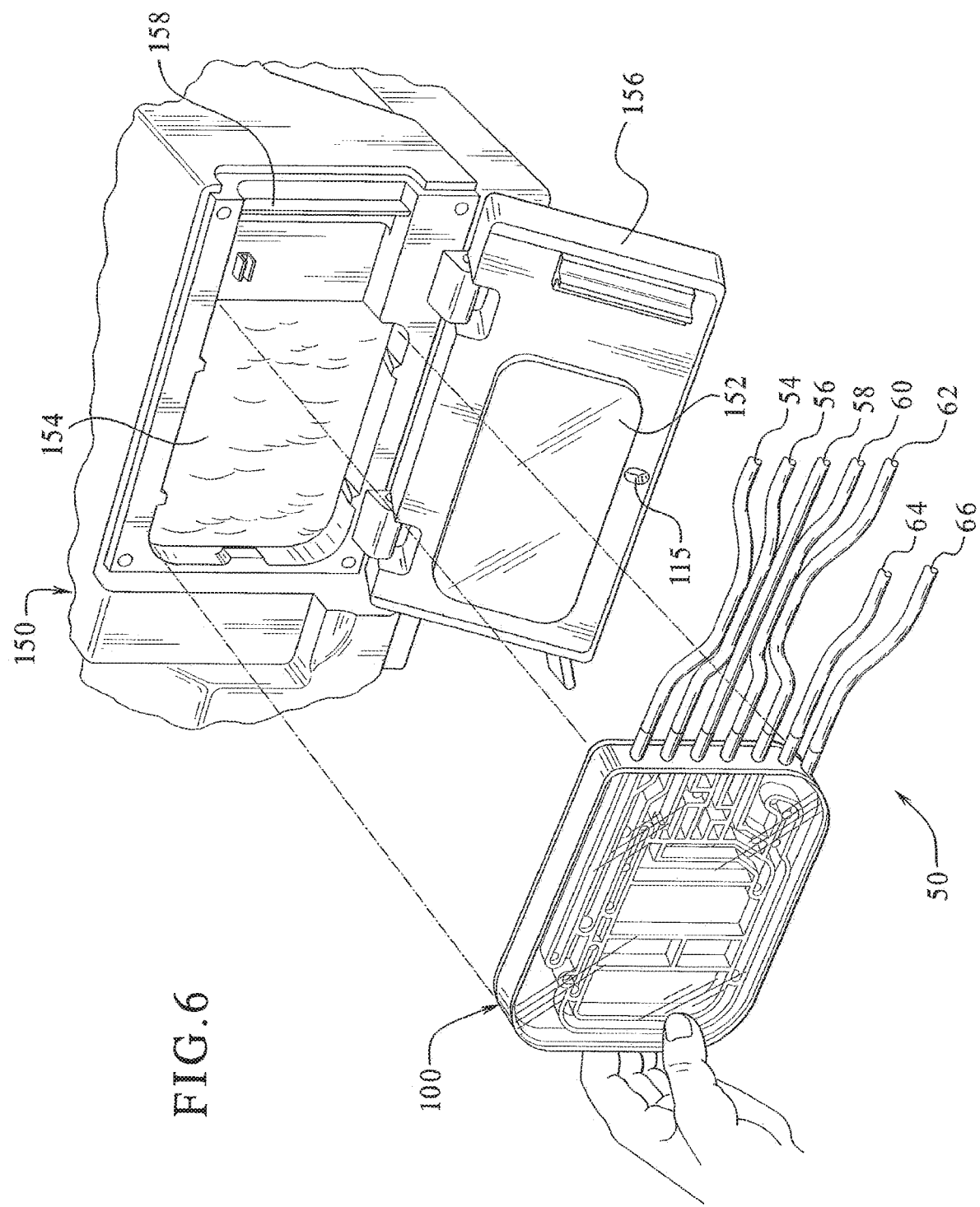
FIG. 6 is a perspective view of one embodiment of a machine that can accept the cassette of the disposable set shown in FIG. 5.

Referring now to the figures and in particular to FIGS. 5 to 9, FIG. 5 illustrates a disposable set 50 that includes a disposable cassette 100 as well as a set of tubes. As shown in the exploded segment 52, the tubing set includes a heater line 54, drain line 56, first proportioning line 58, day/first bag line 60, second proportioning line 62, last fill line 64 and patient line 66. Each of those lines is used with the HomeChoice® machine in one embodiment. It should be appreciated however that other lines associated with other dialysis or medical fluid systems can be used alternatively with the present invention. Automated peritoneal dialysis ("APD") machines, dialysis machines generally or medical fluid machines besides dialysis machines are collectively referred to herein as medical fluid machine 150, which is shown in FIG. 6. More or less lines may also be used without departing from the scope of the invention.

Each of the lines 54 to 66 terminates at a first end at cassette 100 and at a second end at an organizer 42. In operation, machine 150 holds organizer 42 initially at a height that enables a gravity prime to fill fluid at least substantially to the end of at least some of the lines 54 to 66 without filling fluid past connectors located at the end of these lines. Priming is discussed in more detail below.

FIG. 6 illustrates that the cassette 100 and tubes 54 to 66 of set 50 are loaded vertically in one embodiment into machine 150 and held firmly in place between door gasket 152 and diaphragm 154. Door gasket 152 is attached to door 156, which swings open and closed to removably lock cassette 100 in place. Diaphragm 154 provides an interface between the valve and pump actuators, located inside machine 150 behind diaphragm 154, and the valve and pump fluid receiving chambers located in cassette 100.

Figure 7:
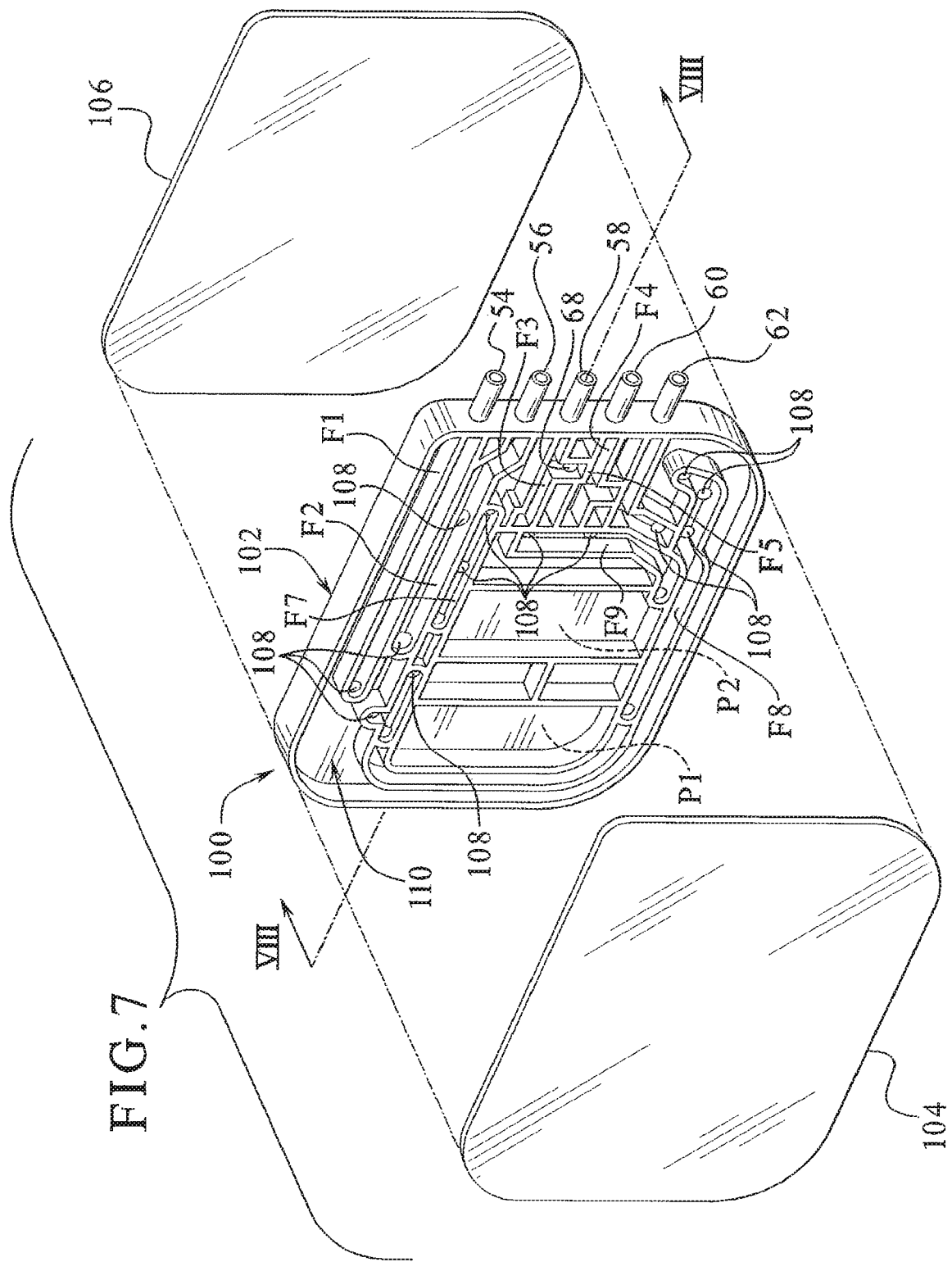
FIG. 7 is a perspective view of the cassette of the disposable set shown in FIG. 5, wherein flexible membranes of the cassette are exploded to show various inner components of the cassette.

FIG. 7 is a perspective view of cassette 100 showing that the cassette 100 includes a housing 102, which is sealed on both sides by flexible membranes 104 and 106. The housing defines a plurality of pump chambers P1 and P2, valves V1 to V10 (which are located on the opposite side of housing 102 from the side shown in FIG. 7), a plurality of flow paths F1 to F9 and a plurality of ports 108 that extend through an interior divider 110 that divides housing 102 and cassette 100 into two separate fluid flow manifolds.

Figure 8:
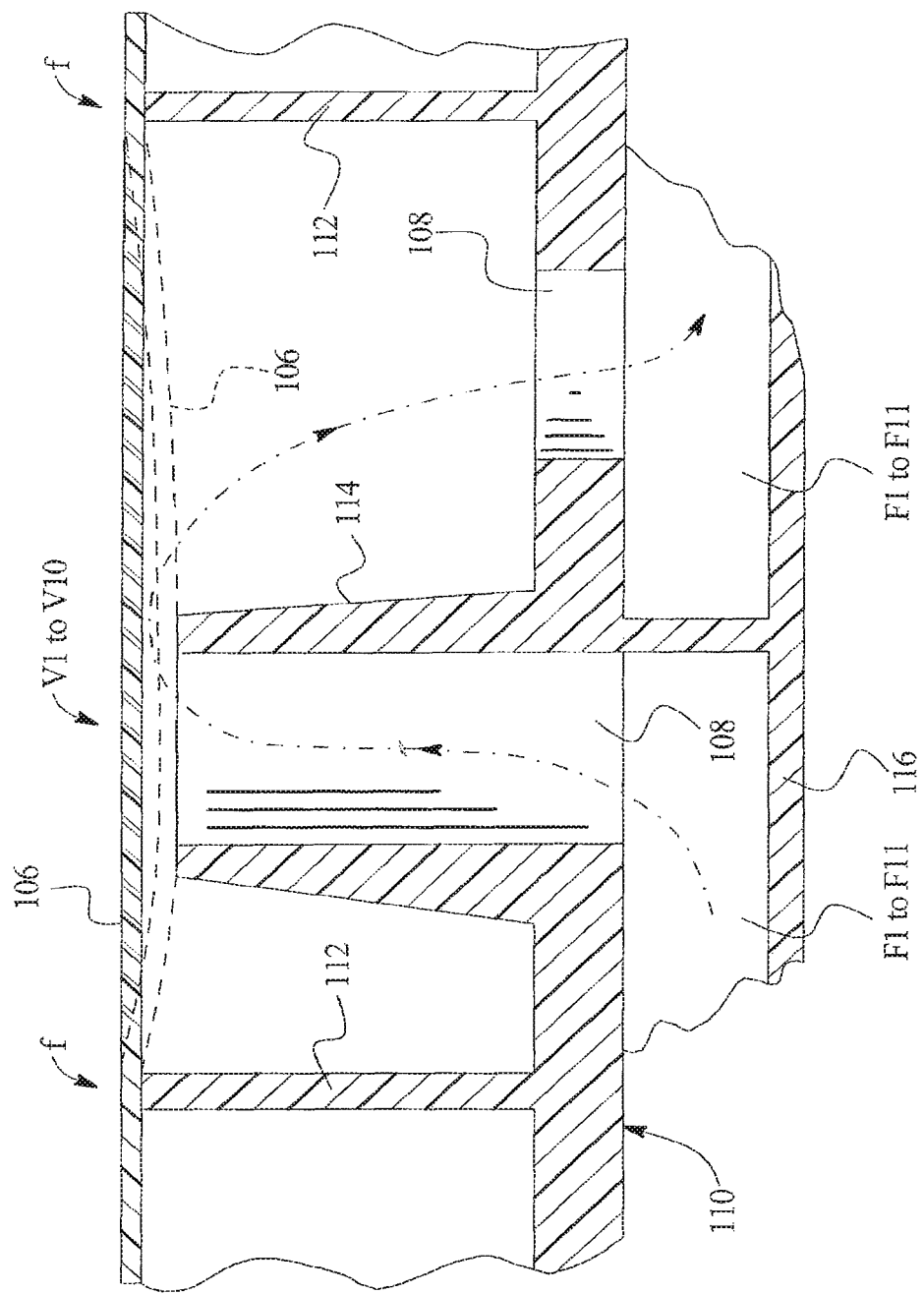
FIG. 8 is a portion of a cross section taken along line VIII-VIII in FIG. 7.

FIG. 8 illustrates a cross-section taken through line VIII-VIII shown in FIG. 7. The cross-section shows membrane 106, divider 110 and a port 108 described above. Additionally, external valve chamber walls 112 and internal valve chamber wall 114 are illustrated, which cooperate to produce one of the valves V1 to V10 on one side of divider 110 of cassette 100. Further, internal chamber wall 114 cooperates with a back 116 (which can also be a flexible membrane) to create various ones of the flow paths F1 to F11 on the other side of divider 110 of cassette 100. Flexible membrane 106 seals to external chamber walls 112 and upon application of a force f to internal chamber walls 114 (to close a fluid connection between a first one of the paths F1 to F11 and a second one of those paths). Upon the release of force f or the application of a vacuum or negative force to membrane 106, membrane 106 is pulled away from internal wall 114, reestablishing the communication between the fluid paths.

Figure 9:
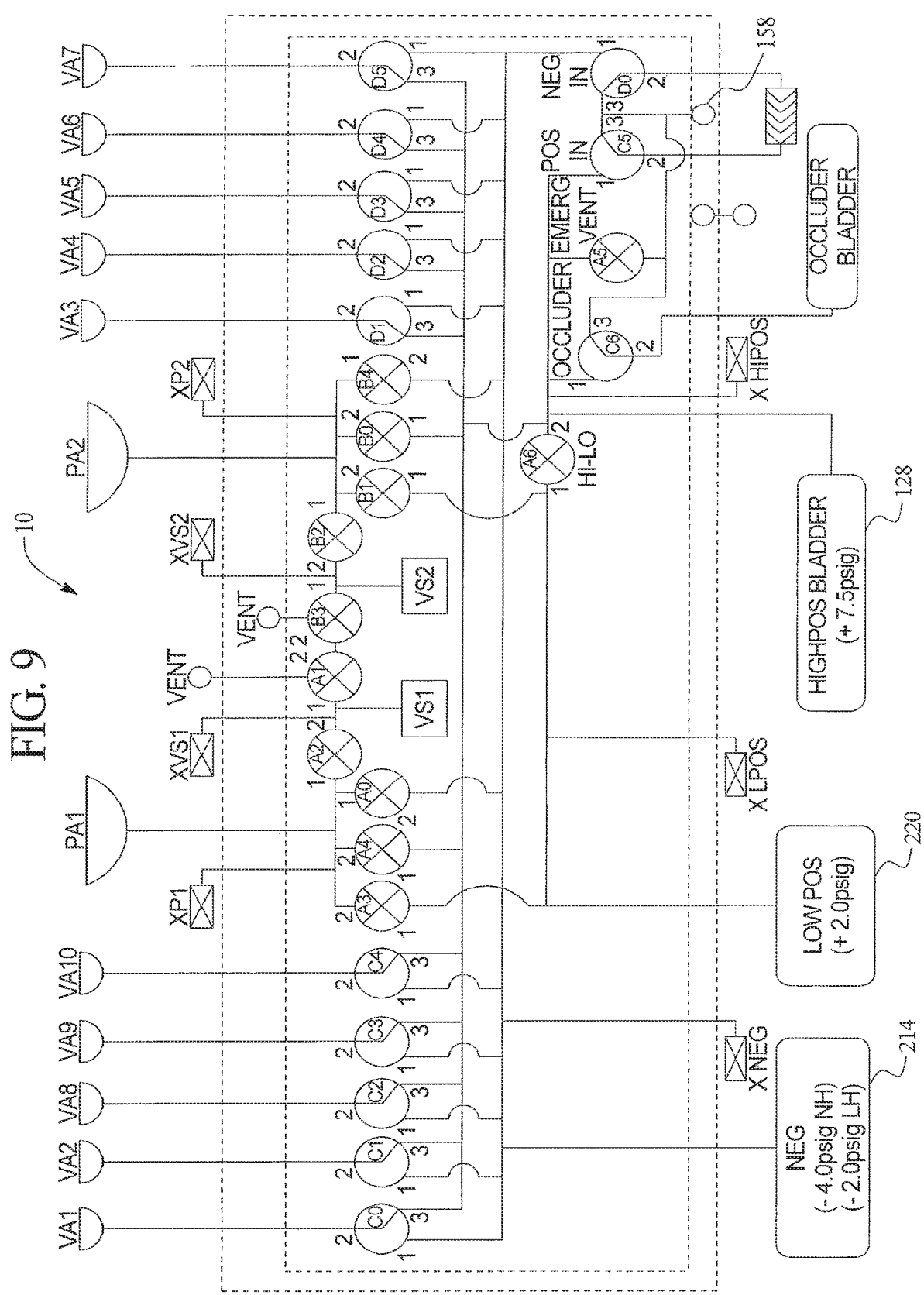
FIG. 9 is a schematic view of one embodiment of a pneumatic operating system for the machine and cassette shown in FIG. 6.

FIG. 9 illustrates a schematic view of a pneumatic control system 10 for a dialysis machine, such as an automated peritoneal dialysis machine is illustrated. FIG. 9 is a schematic of the pneumatic control system employed in the HomeChoice® Automated Peritoneal Dialysis system and is useful for describing the operation of the present invention. It should be appreciated however that the teachings of the present invention are not limited to the HomeChoice® machine nor to only those machines having the same or analogous components. Instead, the present invention describes a test and methodology that is applicable to many different medical fluid systems.

In a set-up portion of the integrity test of the present invention, disposable cassette 100 is loaded into dialysis machine 150. To do so, an air pump (not illustrated) is turned on. That air pump communicates with various pneumatic components illustrated in FIG. 9, including emergency vent valve A5, occluder valve C6, and actuators C0, C1, C2, C3, C4, D1, D2, D3, D4 and D5 for the fluid valves, which causes an occluder 158 (see also FIG. 6) to retract to enable the disposable set 50 and cassette 100 to be loaded into machine 150. Once the set 50 has been loaded, emergency vent valve A5 is closed, so that high positive bladder 128 can be inflated, which seals cassette 100 between the door 156 and diaphragm 154, while maintaining the occluder 158 in an open position (FIG. 6). The remainder of the test is illustrated by FIGS. 10 to 14.

Referring now to FIG. 10, a first step of the test tests the pump chambers P1 and P2 using positive pressure and tests valves V1 to V10 using negative pressure. In particular, the cassette sheeting of cassette 100 over pump chambers P1 and P2 is pressurized to +5 psig using the low positive pressure tank 220 and valves A3 and B1 shown in FIG. 9. A −5 psig vacuum is pulled on the cassette sheeting of cassette 100 over the fluid valves V1 to V10 using negative tank 214 and valves A0 and B4 shown in FIG. 1.

Simultaneous pressure decay tests are then conducted on the: (i) air volume in the low positive tank 220 and pump chambers P1 and P2; and (ii) the air volume in the negative tank 214 and fluid valves V1 to V10. If the pressure decay in the positive pressure system exceeds, e.g., one psig, an alarm is sent displaying a pump chamber sheeting damaged error or code therefore. If the difference in pressure in the negative pressure system exceeds, e.g., one psig, an alarm is sent displaying a fluid valve sheeting damaged error or code therefore. Positive pressure tested areas for this first step are shown in double hatch and negative pressure tested areas are shown in single hatch in FIG. 10.

Importantly, test step one tests cassette 100 from the outside. That is, the pressure is applied to the outside of the sheeting over pump chambers P1 and P2 and negative pressure is applied to the outside of the sheeting over valves V1 to V10. As described below, the remaining test steps apply positive pressure and negative pressure to the sheeting from inside the cassette. The designation of the Figures however is the same, namely, positive pressure tested areas (internal and external) are shown using a double hatch. Negative pressure tested areas (internal and external) are shown using a single hatch. The ports 108 tested in each step are darkened and labeled either "positive pressure tested" or "negative pressure tested".

Referring now to FIG. 11, a second step of the test of the present invention tests the pump chambers P1 and P2, certain fluid pathways and certain valves using positive pressure and negative pressure. The second step begins by evacuating negative tank 214 to −5 psig and opening valve B4 to fill pump chamber P2 in the cassette with air through open fluid valve V7. Next, low positive pressure tank 220 is pressurized to +5 psig and valve A3 is opened to empty pump chamber P1 through open fluid valve V10. Fluid valves V7 and V10 are then closed. Occluder valve C6 is de-energized so that occluder 158 closes, pinching/sealing all fluid lines 54 to 66 exiting cassette 100. Valves A3 and B4 are then closed. Actuator valve B1 is opened with fluid valves V4, V6 and V7 open to pressurize the air in cassette pump chamber P2 and to test the fluid pathways downstream of V4, V6 and V7 for leakage across the occluder 158 and/or across the fluid channels within the cassette. Actuator valve A0 is then opened with fluid valves V1, V2 and V9 open to create a vacuum in cassette pump chamber P1 and to test the fluid pathways downstream of V1, V2 and V9 for leakage across occluder 158 and/or across the fluid channels within the cassette.

Next, a first set of simultaneous pressure decay/rise tests is conducted on low positive pressure tank 222 and negative pressure tank 214. The difference in pressure in both positive pressure tank 220 and negative pressure tank 214 is recorded as well as the final pressure in positive pressure tank 220 and negative pressure tank 214. Valve V3 is opened and a second set of simultaneous pressure decay/rise tests is conducted on low positive pressure tank 220 and negative pressure tank 214 as the contents of pump chamber P2 flow freely into pump chamber P1 through open valves V1 and V3. If the sum of difference in pressures from the first set of pressure decay tests exceeds, for example, two psig, and the sum of the difference in pressure from the second set of tests is less than one psig, an alarm is issued for a cross-talk leakage error. Positive pressure tested areas for the second step are shown in double hatch and with ports 108 so marked and negative pressure tested areas are shown in single hatch and with ports 108 so labeled in FIG. 11.

Referring now to FIG. 12, a third step of the test tests the pump chambers P1 and P2, certain fluid pathways and certain valves using positive pressure and negative pressure. The third step begins by evacuating negative pressure tank 214 to −5 psig and opening valve B4 to fill pump chamber P2 in the cassette with air through open fluid valve V7. Low positive pressure tank 220 is then pressurized to +5 psig and valve A3 is opened to empty pump chamber P1 through open fluid valve V10. Valves V7 and V10 are then closed. Occluder valve C6 is de-energized so that the occluder 158 closes, pinching/sealing all fluid lines exiting cassette 100. Valves A3 and B4 are closed. Pump actuator valve B1 is opened with fluid valves V3, V4 and V6 open to pressurize the air in pump chamber P2 and to test fluid pathways downstream of V3, V4 and V6 for leakage across occluder 158 and/or across the fluid channels within cassette 100. Pump actuator valve A0 is then opened with fluid valves V2, V9 and V10 open to create a vacuum in pump chamber P1 and to test the fluid pathways downstream of V2, V9 and V10 for leakage across the occluder 158 and/or across the fluid channels within cassette 100.

Next, a first set of simultaneous pressure decay/rise tests is conducted on low positive pressure tank 222 and negative pressure tank 214. The difference in pressure in both positive tank 220 and negative tank 214 is recorded as well as the final pressure in positive pressure tank 220 and negative pressure tank 214. Valve V1 is opened and a second set of simultaneous pressure decay/rise tests is conducted on low positive pressure tank 220 and negative pressure tank 214 as the contents of pump chamber P2 flow freely into pump chamber P1 through open valves V1 and V3. If the sum of the difference in pressure from the first set of pressure decay tests exceeds, for example, 2 psig, and the sum of the difference in pressure from the second set of tests is less than one psig, a cross-talk leakage error alarm or code therefore is sent. Positive pressure tested areas for the third step are shown in double hatch and with ports 108 so marked and negative pressure tested areas are shown in single hatch and with ports 108 so marked in FIG. 12.

Figure 13:
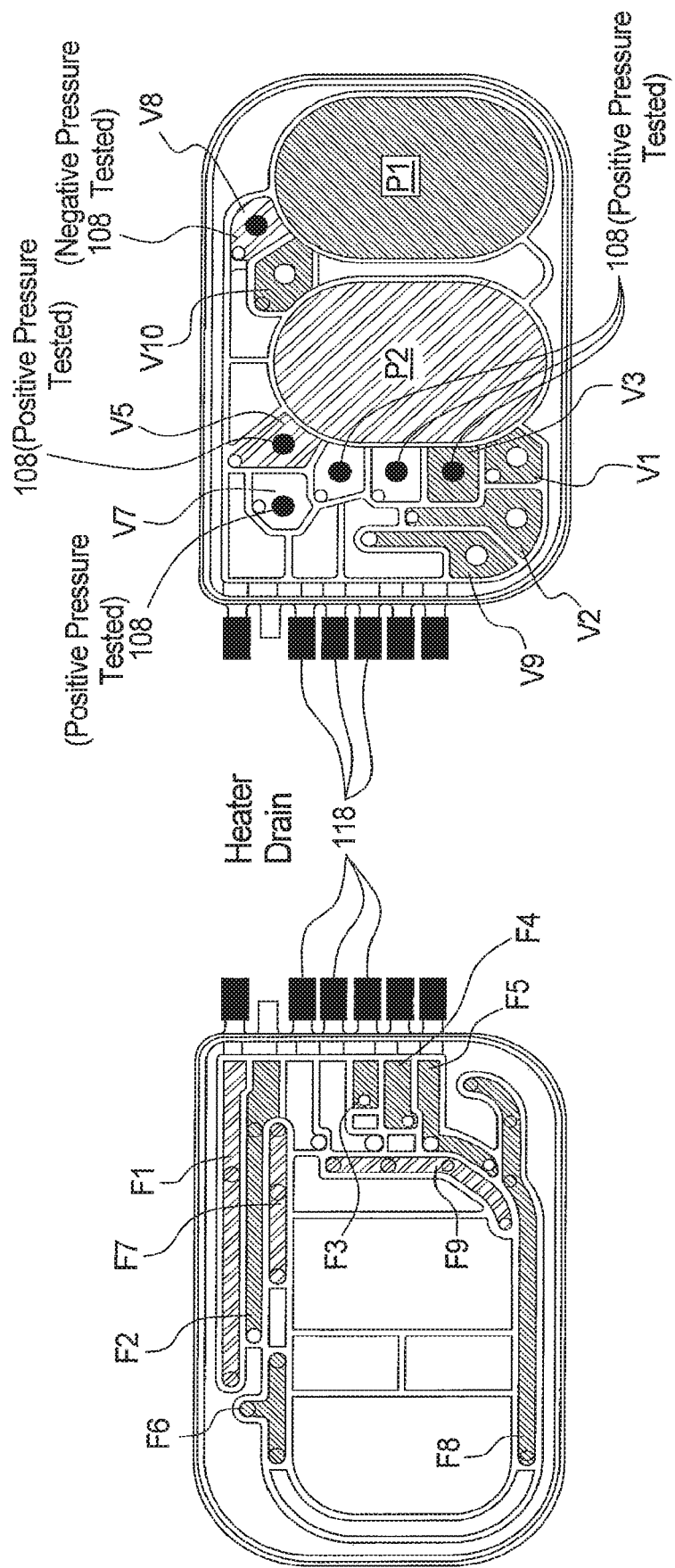

Referring now to FIG. 13, a fourth step of the test tests the pump chambers P1 and P2, certain fluid pathways and certain valves using positive pressure and negative pressure. The fourth step begins by evacuating negative pressure tank 214 to −5 psig and opening valve B4 to fill pump chamber P2 in cassette 100 with air through open fluid valve V7. Low positive pressure tank 220 is pressurized to +5 psig and valve A3 is opened to empty pump chamber P1 through open fluid valve V10. Fluid valves V7 and V10 are closed. Occluder valve C6 is de-energized so that the occluder 158 closes, pinching/sealing fluid lines 54 to 66 exiting cassette 100. Valves A3 and B4 are closed. Pump actuator valve B1 is opened with fluid valve V5 open to pressurize the air in pump chamber P2 and to test the fluid pathways downstream of V5 for leakage across the occluder 158 and/or across the fluid channels within cassette 100. Pump actuator valve A0 is opened with fluid valves V1, V2, V9 and V10 open to create a vacuum in pump chamber P1 and to test the fluid pathways downstream of V1, V2, V9 and V10 for leakage across the occluder 158 and/or across the fluid channels within the cassette.

Next, a first set of simultaneous pressure decay/rise tests is conducted on low positive pressure tank 222 and negative pressure tank 214. A difference in pressure in both positive tank 220 and negative tank 214 is recorded as well as the final pressure in positive pressure tank 220 and negative pressure tank 214. Valve V3 is opened and a second set of simultaneous pressure decay/rise tests is conducted on low positive pressure tank 220 and negative pressure tank 214 as the contents of pump chamber P2 flow freely into pump chamber P1 through open valves V1 and V3. If the sum of the difference in pressure from the first set of pressure decay tests exceeds, for example, 1.5 psig, and the sum of the difference in pressure from the second set of tests is less than 0.75 psig, a cross talk leakage error alarm or code is sent and displayed. Positive pressure tested areas for the forth step are shown in double hatch and with ports 108 so marked and negative pressure tested areas are shown in single hatch and with ports so marked 108 in FIG. 13.

Figure 14:
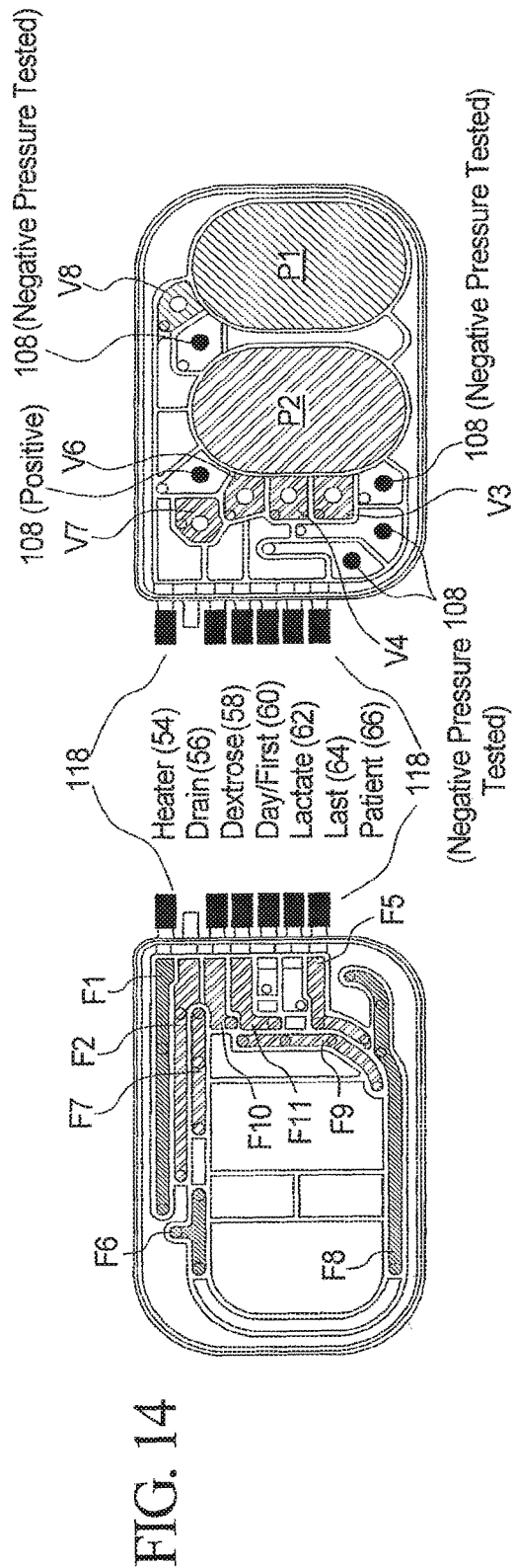

Referring now to FIG. 14, a fifth step of the test tests the pump chambers P1 and P2, certain fluid pathways and certain valves using positive pressure and negative pressure. The fifth step begins by evacuating negative pressure tank 214 to −5 psig and opening valve B4 to fill pump chamber P2 in cassette 100 with air through open fluid valve V7. Low positive pressure tank 220 is pressurized to +5 psig and valve A3 is opened to empty pump chamber P1 through open fluid valve V8. Fluid valves V7 and V10 are closed. Occluder valve C6 is de-energized so that the occluder 158 closes, pinching/sealing fluid lines 54 to 66 exiting cassette 100. Valves A3 and B4 are closed. Pump actuator valve B1 is opened with fluid valves V3, V4, V6 and V7 open to pressurize the air in pump chamber P2 and to test the fluid pathways downstream of V3, V4, V6 and V7 for leakage across the occluder 158 and/or across the fluid channels within cassette 100. Pump actuator valve A0 is opened with fluid valve V8 open to create a vacuum in pump chamber P1 and to test the fluid pathways downstream of V8 for leakage across the occluder 158 and/or across the fluid channels within the cassette.

Next, a first set of simultaneous pressure decay/rise tests is conducted on low positive pressure tank 222 and negative pressure tank 214. A difference in pressure in both positive tank 220 and negative tank 214 is recorded as well as the final pressure in positive pressure tank 220 and negative pressure tank 214. Valve V1 is opened and a second set of simultaneous pressure decay/rise tests is conducted on low positive pressure tank 220 and negative pressure tank 214 as the contents of pump chamber P2 flow freely into pump chamber P1 through open valves V1 and V3. If the sum of the difference in pressure from the first set of pressure decay tests exceeds, for example, 1.5 psig, and the sum of the difference in pressure from the second set of tests is less than 0.75 psig, for example, a cross talk leakage error alarm or code is sent and displayed. Positive pressure tested areas for the fifth step are shown in double hatch and with ports 108 so marked and negative pressure tested areas are shown in single hatch and with ports 108 so marked in FIG. 14.

In each of test steps two through five of FIGS. 11 to 14 described above, pump chamber P2 is filled with air and pump chamber P1 is evacuated before the pressure decay/vacuum rise tests are performed. Those tests are improved when chamber P2 is pressurized above atmospheric pressure as opposed to merely maintaining the chamber at atmospheric pressure. For one reason, maintaining chamber P2 at a positive compensates for the slight compressibility of air in the chamber when the test steps are commenced. To pressurize chamber P2, air can be pushed from chamber P1 to P2 with the occluder 158 closed. When P2 is pressurized, occluder 158 is opened, enabling chamber P1 to be evacuated. Pressurized chamber P2 should show very little pressure drop unless a leak in one of the tested pathways is detected.

Figure 15:
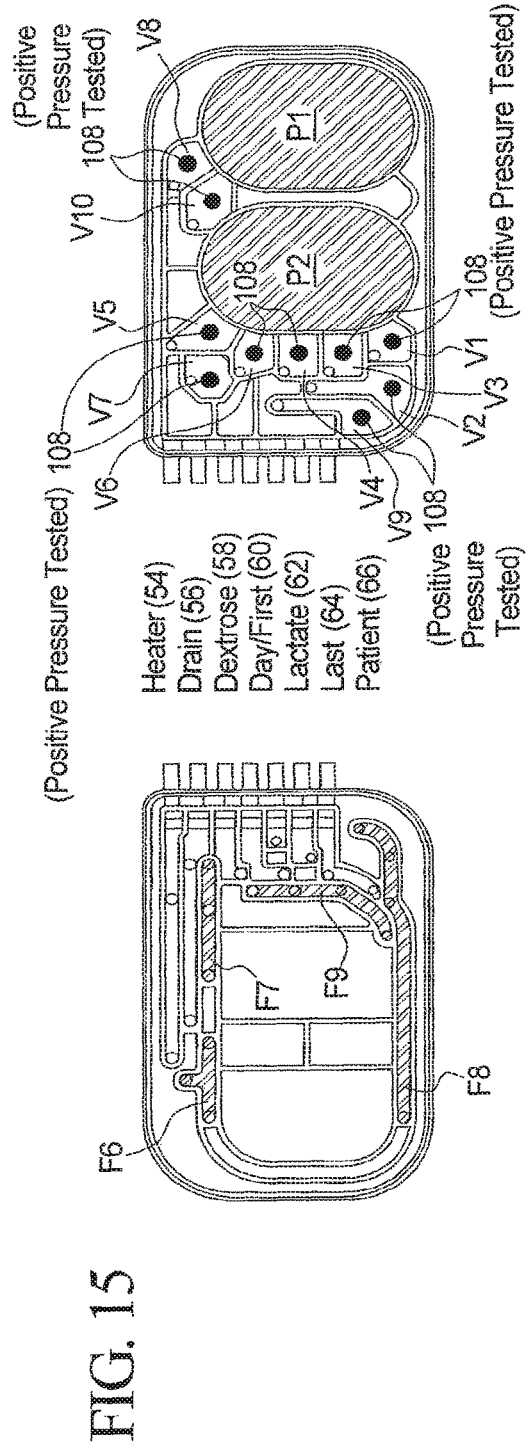

Referring now to FIG. 15, a sixth step of the test of the present invention tests the pump chambers P1 and P2, certain fluid pathways and certain valve ports 108 using positive pressure. To begin the sixth step, a −5 psig vacuum is pulled on the cassette sheeting over the two pump chambers P1 and P2 with all fluid valves except for drain valves V7 and V10 de-energized (closed), so that pump chambers P1 and P2 fill with air. Valves V7 and V10 are closed and the sheeting over pump chambers P1 and P2 of cassette 100 is pressurized to +5 psig using low positive tank 220 and valves A3 and B1. A first pressure decay test is then conducted on the pump chambers P1 and P2, fluid flow paths F6, F7, F8 and F9 and the darkened fluid ports 108 so marked within cassette 100 by monitoring the pressure in the low positive tank 220. If the difference in pressure in the low positive tank 220 exceeds, e.g., one psig, an alarm is sent displaying a fluid valve leaking error or code therefore.

Occluder valve C6 is de-energized so that occluder 158 closes, pinching/sealing all fluid lines 54 to 66 exiting cassette 100. All of valves V1 through V10 except for V5 and V8 are opened and a second pressure decay test is conducted by monitoring the pressure in low positive tank 220. If the difference in pressure in the low positive tank 220 exceeds, e.g., one psig, the sixth series of tests must be repeated. If the difference in pressure in the low positive tank 220 exceeds, e.g., one psig a second time, a an alarm is sent displaying occluder failed. Finally, the occluder is opened and a third pressure decay test is conducted by monitoring the pressure in low positive tank 220. Test step six verifies that tests one and two have not failed if the difference in pressure exceeds, e.g., one psig. Positive pressure tested areas for the sixth step are shown in double hatch and with ports 108 so marked in FIG. 15.

The previous six test steps complete one embodiment of the dry integrity test of the present invention. Viewing the outcome of steps 1 to 4 of the prior art test in FIGS. 1 to 4, it should be appreciated that step 1, shown in FIG. 10 of the dry disposable integrity test of the present invention, tests the equivalent components of all four steps of the original dry integrity test.

Importantly, test steps two to six test the cassette from the inside. That is, positive pressure is applied inside the cassette to the inside of the cassette sheeting and negative pressure is applied inside the cassette to the inside of the cassette sheeting. The positive and negative pressure applied inside the cassette to the inside of the cassette sheeting is created by initially applying pressure (positive or negative) to the outside of the cassette and switching the valves to create the desired pressure distribution inside the cassette as described above.

The first five of the test steps (FIGS. 10 to 14) can be performed with the tip protectors placed on lines 54 through 66 and with the clamps closed on all of the lines except for drain line 56. The tip protectors, shown figuratively as caps 118 on the respective ports of cassette 100, are actually at the ends of tubes 54, 58, 60, 62, 64 and 66. The drain line 56 has a bacteria retentive tip protector that passes to atmosphere air that leaks through the membranes 104 and 106 (FIGS. 7 and 8) or from housing 102, lowering the pressure in the system so that a leak can be detected. The tip protectors are removed when solution bags are connected to the tubes prior to test step six in the series of six test steps. As seen in the prior steps 2 to 4 of FIGS. 2 to 4, all tip protectors have to be removed for those test steps. In the prior art therefore, when a cassette fails during any of the tests illustrated FIGS. 2 to 4, non-sterile air is introduced into the solution bags, causing the solution bags and the cassette to be discarded.

Test steps two through five of the present invention (FIGS. 11 to 14, respectively) test, using air within cassette 100, the same areas of the cassette as does the prior art wet leak test described above. Because steps (i) through (v) of the prior art wet leak test require fluid, solution bags must be attached to obtain such fluid. The present invention eliminates that necessity.

Test step one of the present invention is able to leave the tip protectors connected to all lines except the drain line because the valves are tested in the open position rather than the closed position. When valves V1 to V10 are open, all of the fluid channels F1 to F11 in cassette 100 are in direct communication with both pump chambers P1 and P2 and the drain line. The drain line has a bacteria retentive tip protector that allows air to pass through it, e.g., is fitted with a hydrophobic membrane. Air from a failed test can therefore pass through the drain line from cassette 100, changing the pressure in the system so that a leak can be detected.

Test steps two through five of the disposable integrity test of the present invention are able to leave the tip protectors in place because one part of the system is pressurized while the other is evacuated. Air leaking from the positively pressurized part of cassette 100 to the evacuated part is readily detectable as is air escaping from or leaking into cassette 100. Because air flows more readily than does water or solution through a leak, the air test is more expedient and sensitive than a fluid based test, increasing accuracy and repeatability and decreasing test time.

Test steps two through five of the present invention include a redundant pressure decay test that verifies the results of the first pressure decay test. All four test steps two through five look for leaking flow from a pressurized section of cassette 100 to an evacuated section of the cassette 100. If a leak arises between the two sections of the cassette, the pressure in the two sections should tend towards equilibrium when air flows from the high pressure section to the evacuated section. The redundant test opens valves between the positive and negative sections at the completion of the first pressure decay test to verify that there is a larger pressure change if no leaks exist or a minimal pressure change if a leaks exists.

A failure of occluder 158 to properly crimp tubing lines 54 to 66 does not materially affect the results for test steps two to five because the tip protectors are in place and would otherwise seal all of the lines that are being tested. Additionally, the users/patients are instructed to close the line clamps on all but the drain line when loading set 50 into machine 150. Test step six, which tests the cassette valves V1 through V10 and the occluder 158, can be conducted dry or wet since the solution bags have been connected. The dry test would have to be pressure based, whereas the fluid test could be either pressure or volume based.

The user can clamp the drain line on the disposable set when instructed to do so after an integrity test failure when using the method of the present invention and run the disposable integrity tests again. If the tests do not show a failure a second time (for many of the failure modes), the disposable set can be held responsible for the leak and not the machine 150, e.g., the machine's pneumatic system and/or cassette/machine interface. That feature is useful when a patient seeks troubleshooting assistance. Determining that the machine 150 is working properly and that the cassette 100 is causing the failure precludes swapping a patient's machine needlessly after an integrity failure because of uncertainty about whether the cassette 100 or machine 150 is responsible for the test failure. Conversely, if the tests show a failure a second time, the machine 150 and/or the cassette/machine interface can be held responsible for the leak.

While cassette 100 is illustrated with pump chambers P1 and P2, valve chambers V1 to V10, associated ports 108, and fluid paths F1 to F11, it should be appreciated that the method of the invention is equally applicable to cassettes and actuating systems that have different pump and valve geometries than the ones shown as well as additional features, such as heaters, pressure sensors, temperature sensors, concentration sensors, blood detectors, filters, air separators, bubble detectors, etc. The cassettes can be rigid with a single side of sheeting, be rigid with dual sided sheeting, have dual sheets forming fluid pathways, have a rigid portion connected to a flexible portion, etc. The cassettes are useable in any medical fluid delivery application, such as peritoneal dialysis, hemodialysis, hemofiltration, hemodiafiltration, continuous renal replacement therapy, medication delivery, plasma pherisis, etc., and any combination thereof.

Figure 16:
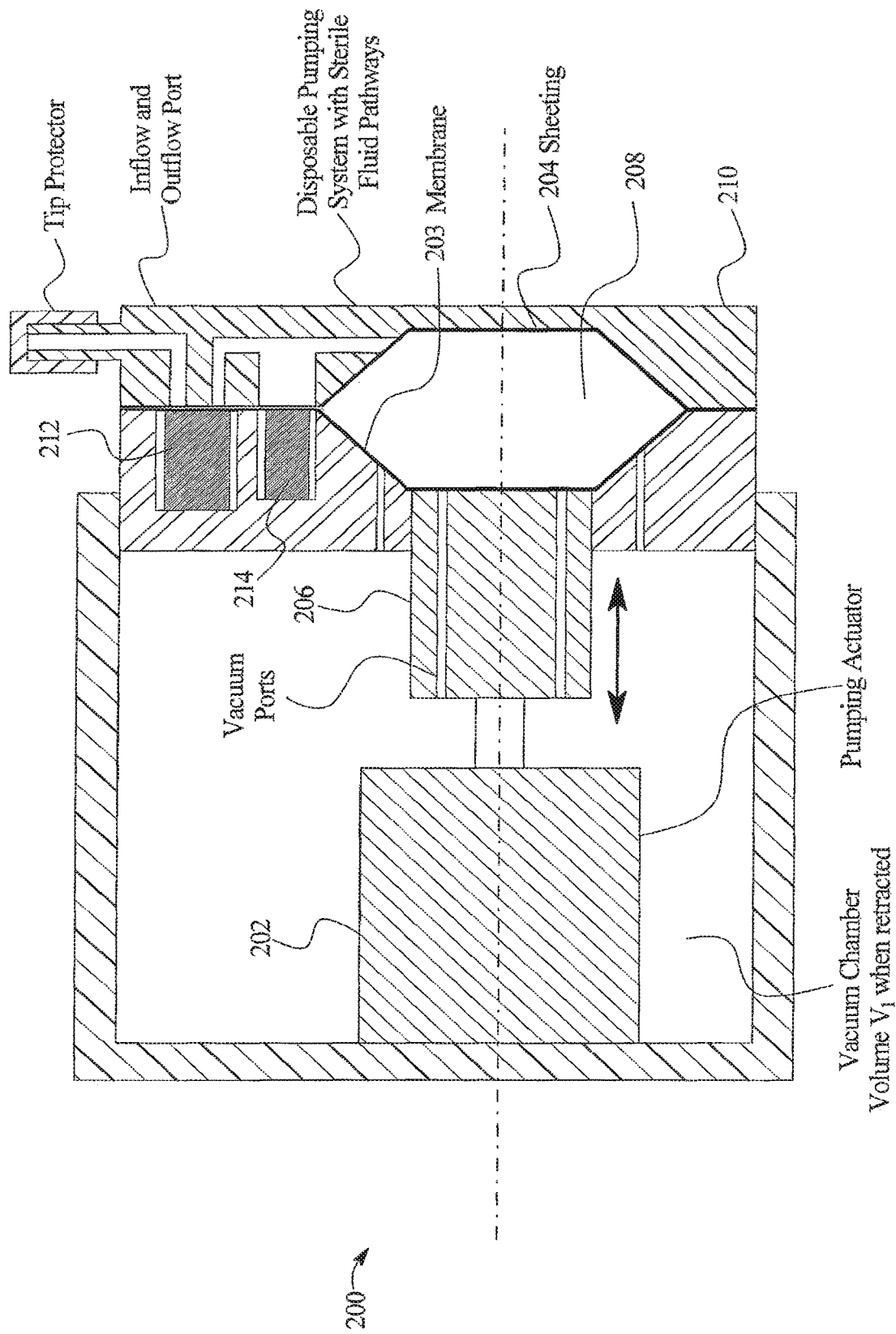
FIG. 16 is a schematic illustration of an alternative medical fluid machine that employs mechanical positive pressure actuation versus pneumatic pressure.

FIG. 16 shows one alternative embodiment of the present invention via system 200, wherein the pneumatic source of positive pressure used above is replaced by a mechanical actuator 202 that pushes a flexible membrane film 203. Film 203 is attached to a cassette 210 with sheeting 204 on one side of thereof. System 200 uses a vacuum to force the membrane 203 to follow a piston head 206 when head 206 retracts from or moves toward cassette 210. While no external source of positive pressure is provided, air can be drawn into pumping chamber 208, while fluid valve 212 is closed and actuator 202 and head 206 are moved forward to generate an internal pressure that is used to perform the disposable integrity tests described herein. A pressure sensor 214 is provided in one embodiment to perform the pressure decay tests. The position of actuator 202 and head 206 can also be used to perform a leak test by applying a constant force. The actuator and head should remain stationary when a constant force is applied if no leak is present. Forward motion would indicate that there is a leak in the system being tested.

Appendix A shows data from step one of the integrity test of the present disclosure. Appendix B also shows data from step one of the integrity test of the present disclosure. In Appendix B, the bolded, larger font size data shows when defects were detected. It is noteworthy that for fifty different cassettes tested and known to be defective, all fifty defects were detected. When the drain line was clamped after the software instructed the operator to do so, forty-seven of the fifty tests no longer failed indicating that the leak was in the cassette and not the therapy machine. The other three of the fifty clamped tests were inconclusive. Those three are marked in bolded italics. It is also noteworthy that one cassette appears to have two defects and is highlighted in bold italics as well.

For the test, ten defects were created in the pump chamber sheeting and forty defects were created in the valve sheeting. All pump chamber tests were run with positive pressure and all valve sheeting tests were run with negative pressure. The defects were punctures and slits made by a 0.035 inch (0.89 mm) outside diameter hot needle or an Exacto knife with a stop positioned to create consistent slits of 0.125 inch (3.2 mm).

Appendix C shows data from the integrity test step two of the present disclosure. The positive pressures represent pressures inside pump chamber P2, as measured by pressure sensors monitoring positive tank 220 (FIG. 9). The negative pressures are for pressures inside pump chamber P1, as measured by the pressure sensors monitoring negative tank 214 (FIG. 9). Cassettes predisposed with a number of defects were tested as well as some cassettes without known defects. Some of the defects were not detected by test step two. Test steps three, four and five did however reveal the defects that test step two did not.

Improved Priming Method and Apparatus

Turning to the priming method and apparatus of the present invention, the method and apparatus are advantageous in a number of respects. First, the method employs the pumps of the medical fluid machine 150 shown above in FIG. 6 to pump priming fluid for an initial portion of the prime to dislodge air bubbles that typically become trapped, for example, in the patient line 66, near cassette 100. Second, the method uses software contained within the controller of machine 150 that expects to see a particular pressure drop when the medical fluid pump (or pumps) pushes the initial priming fluid. If the expected pressure drop is not seen, machine 150 assumes there is a clamp on the priming or patient line, responds accordingly and sends a suitable error message or code.

Figure 17:
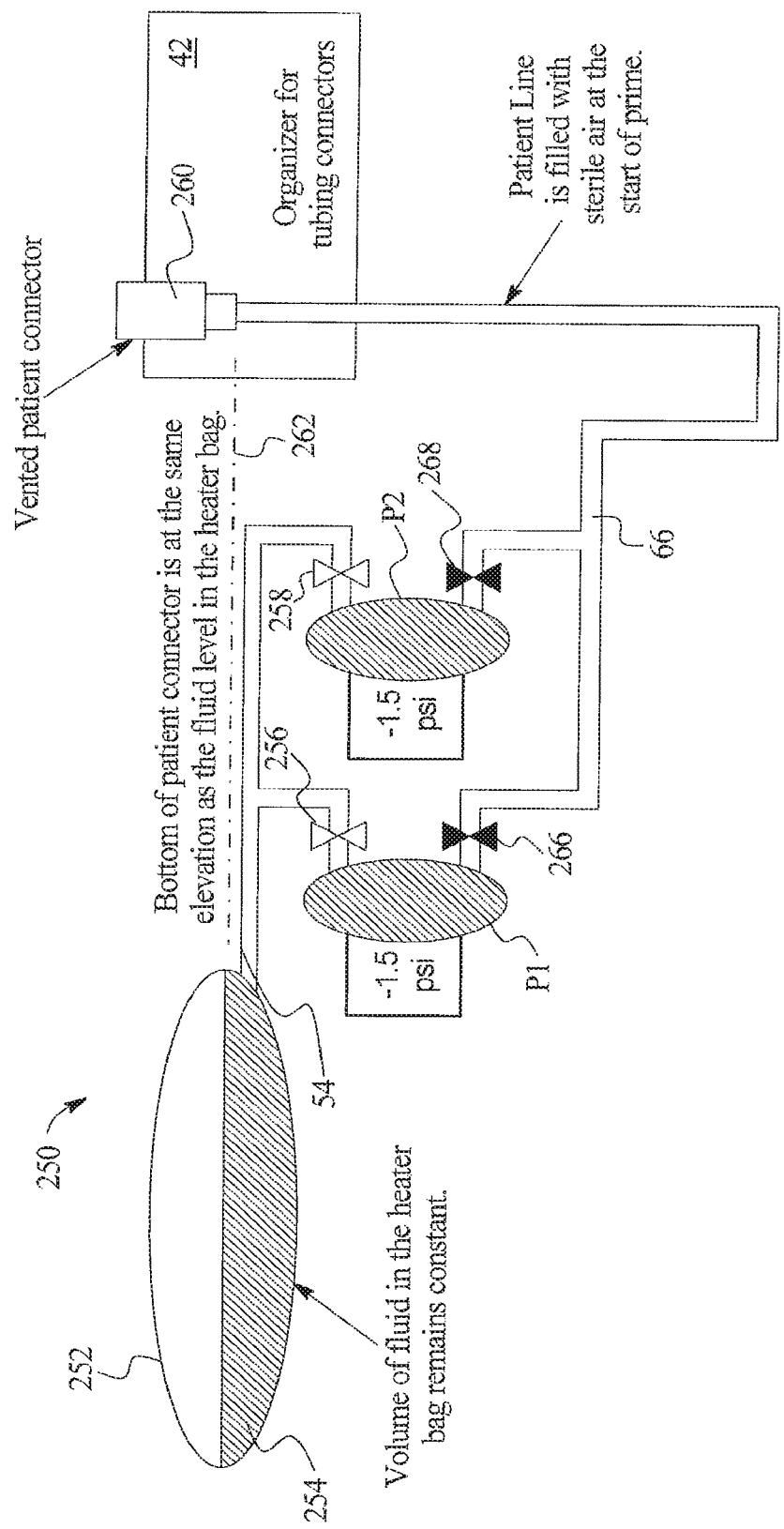
FIGS. 17 to 22 are schematic views illustrating one apparatus and method of the present invention for priming a medical fluid system.

Referring now to FIG. 17, an initial schematic of an apparatus 250 for performing the priming method of the present invention is shown. The apparatus includes a supply bag 252 filled with a volume of fluid 254. A line from solution bag 252 to pumps P1 and P2 is provided. In most instances, that line is the heater bag line 54 shown in FIGS. 5 and 17, which enters cassette 100 that houses pump chambers P1 and P2. Valves 256 and 258 selectably allow fluid 254 to pass via line 54 to pump chambers P1 and P2, respectively. A priming line is provided from pump chambers P1 to P2 to a distal end of the line, which is provided with a vented distal end connector 260. Normally, the primed line is the patient line shown as line 66 in FIGS. 5 and 17. It should be appreciated, however, that the priming line may be a different line than the patient line. Moreover, the priming apparatus 250 and associated method is applicable to systems that prime multiple lines sequentially or simultaneously.

Connector 260 as illustrated is positioned in organizer 42 discussed above in connection with FIG. 5. The positioning of connector 260 is set so that the prime stops at a desired point at the beginning of or in the interior of connector 260. That level as shown by line 262 is the same level as the height of fluid 254 in container 252. Valves 266 to 268 are provided between pumps P1 and P2 and connector 260 to selectively allow fluid to enter patient line or priming line 66.

The first step of the priming method shown in FIG. 17 is to close valves 266 and 268 (black) and open valves 256 and 258 (white). Such valve arrangement enables fluid 254 to gravity feed or be drawn in by pumps P1 and P2 (the −1.5 psig shown in FIG. 17 symbolizes the suction being applied to the flexible pump film as fluid is drawn into the pump chamber) from container 252 and fill pump chambers P1 and P2. Because valves 266 and 268 are closed, no fluid enters priming line 66.

Figure 18:
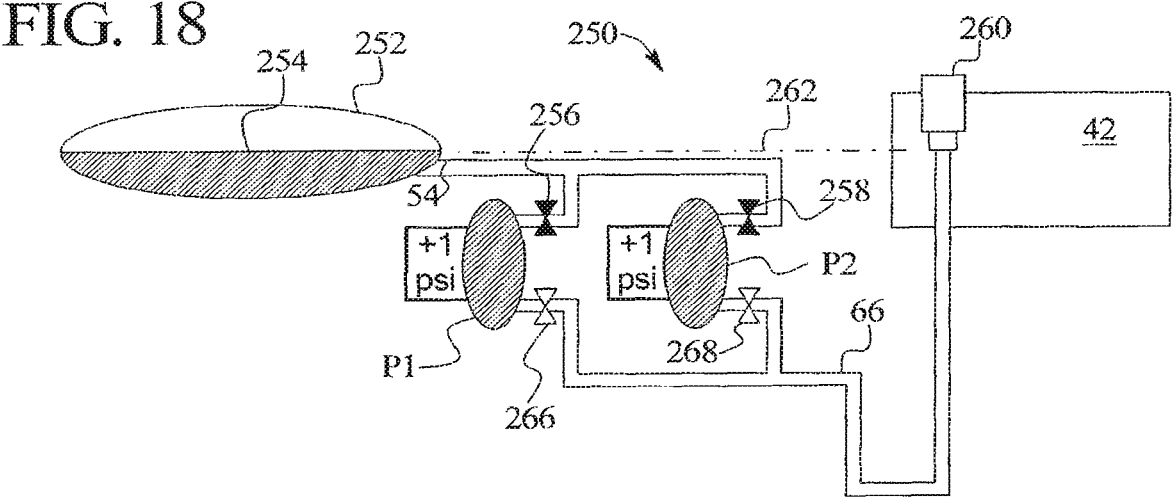

FIG. 18 illustrates a second step of the priming method of the present invention. In FIG. 18, valves 256 and 258 are closed (black), so that no additional fluid can flow via heater bag line 54 from container 252 to pump chambers P1 and P2. Next, a 1.0 psig pressure is applied to the flexible pump film, pressing the film against the fluid in pump chambers P1 and P2. Valves 266 and 268 are then opened (white) so that fluid communication exists between pump chambers P1 and P2, priming or patient line 66 and connector 260.

Figure 19:
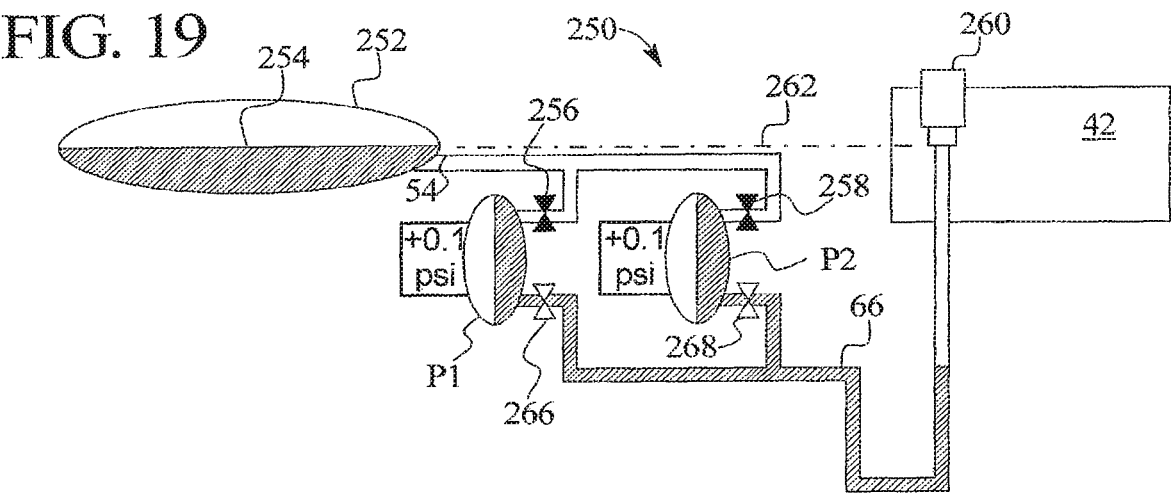

FIG. 19 illustrates that after pressurizing the pump chambers P1 and P2, fluid flows from those chambers through an initial portion of patient or priming line 66. The pressure inside pump chambers P1 and P2 falls accordingly, e.g., to about 0.1 psig, as this fluid is displaced from the pump chambers and the volume of air pushing against the pump film expands. The fluid pumped from chambers P1 and P2 is not meant to extend all the way to connector 260, rather, the pumped fluid is intended to flow through any trapped air at the proximal end of patient line 66, so that such air is not an impediment to priming. Therefore, the fluid volume drawn into pump chambers P1 and P2 should be less than the volume inside patient line 66 extending from cassette 100 to connector 260.

The volume of liquid that does fill patient line 66 via the pump stroke of chambers P1 and P2 does, however, push some air through vented connector 260, leaving the line partially filled with solution and partially filled with air, wherein the air is collected at the distal end and the solution resides at the proximal end of line 66. This method of dislodgement works regardless of how many extensions are added to patient line 66. Older priming sequences had varied results depending upon whether a standard or non-standard length of patient line was used. The present method is independent of patient line length and can be used with a heater bag containing as little as 1000 ml of solution as seen in Table 1.

TABLE 1

Patient Line Priming Height

|  | 1000 ml heater bag volume | 6000 ml heater bag volume | 1000 ml heater bag volume |
|---|---|---|---|
| | Average Primed Height Above Table | | |
| Set with no patient extension line | 7.17 | 7.8 | 6.28 |
| Set with 1 patient extension line | 6.8 | 7.95 | 6.34 |
| Set with 2 patient extension lines | 6.5 | 7.88 | 6.23 |
| | Standard Deviation in Primed Height Above Table | | |
| Set with no patient extension line | 0.52 | 0.16 | 0.27 |
| Set with 1 patient extension line | 1.35 | 0.16 | 0.11 |
| Set with 2 patient extension lines | 0.5 | 0.13 | 0.23 |

Figure 20:
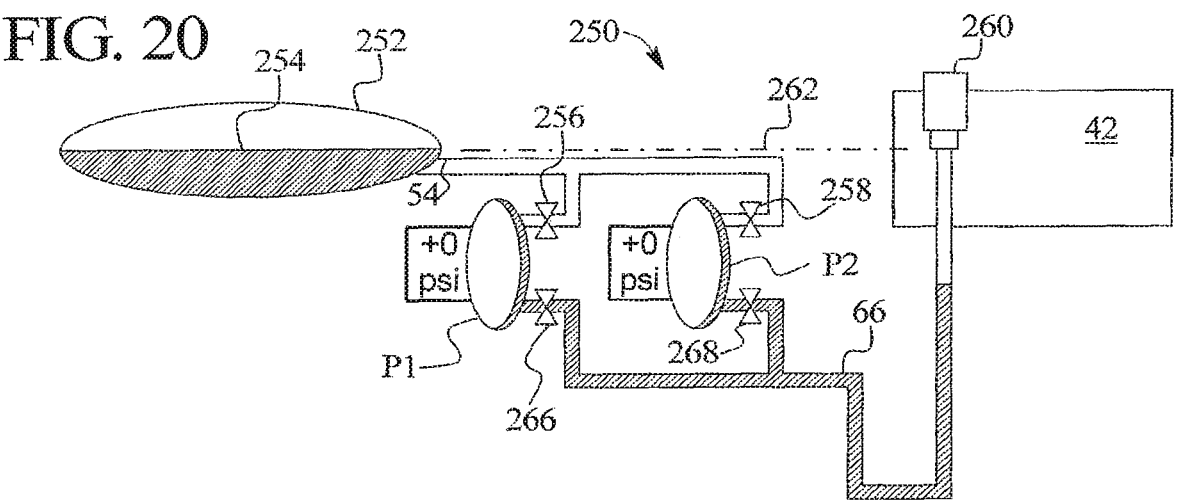
Figure 21:
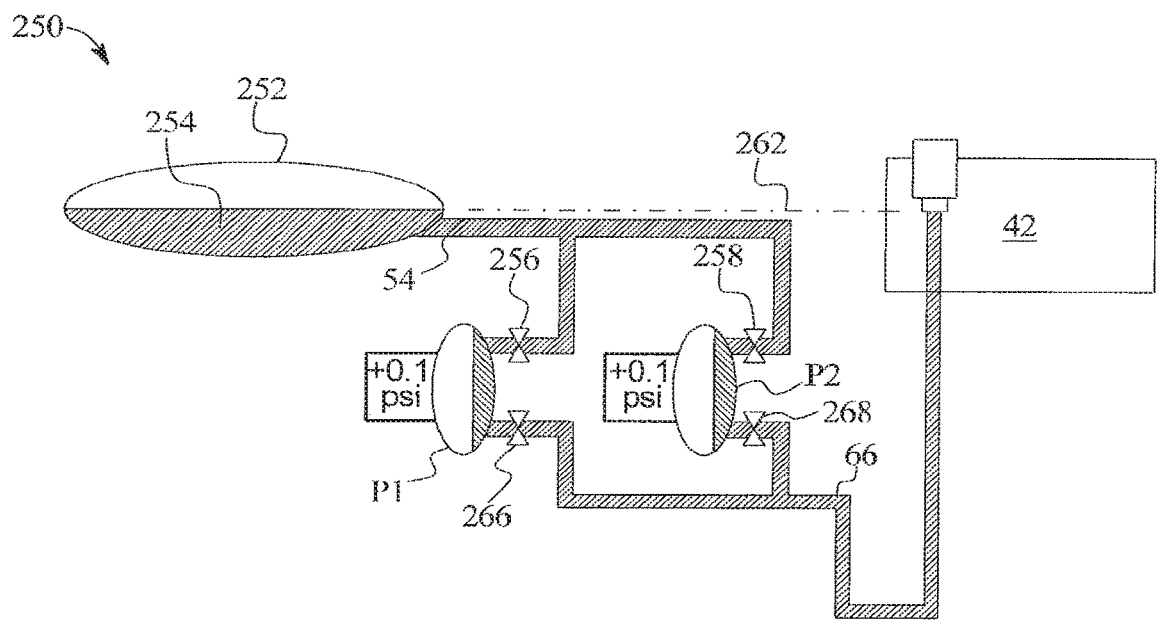

FIGS. 20 and 21 illustrate the final step in the priming method associated with apparatus 250. Here, inlet valves 256 and 258 are opened, while outlet valves 266 and 268 are left open.

In FIG. 20, any fluid in pump chambers P1 and P2 not pumped in FIG. 19 is allowed to flow via gravity from such pump chambers into patient line 66. Additionally, fluid 254 is enabled to gravity flow from container 252 to complete the patient line prime. In FIG. 20, the pressure in chambers P1 and P2 can drop to near zero psig as any remaining pressure from the pump stroke in FIG. 19 is dissipated. FIG. 21 shows that the patient or priming line 66 is fully primed, with the level of fluid 254 reaching the elevational height 262 of the fluid 254 remaining in bag 252. The level of fluid inside pump chambers P1 and P2 will also reach some equilibrium which may be at a slight positive pressure within those chambers. That is, the pressure in the pump chamber will equalize with the head pressure of patient line 66 and fill bag 252.

If the patient line 66 is inadvertently clamped during priming, the pressure in pump chambers P1 and P2 in the step illustrated by FIG. 19 does not fall below an expected level, e.g., from the one psig shown in FIG. 18 to 0.1 psig shown in FIG. 19. The pressure instead remains at a higher level, such as 0.5 psig. The controller inside machine 150 senses that discrepancy and prompts the patient via a visual, audio or audiovisual message to unclamp the patient or priming line 66.

Figure 22:
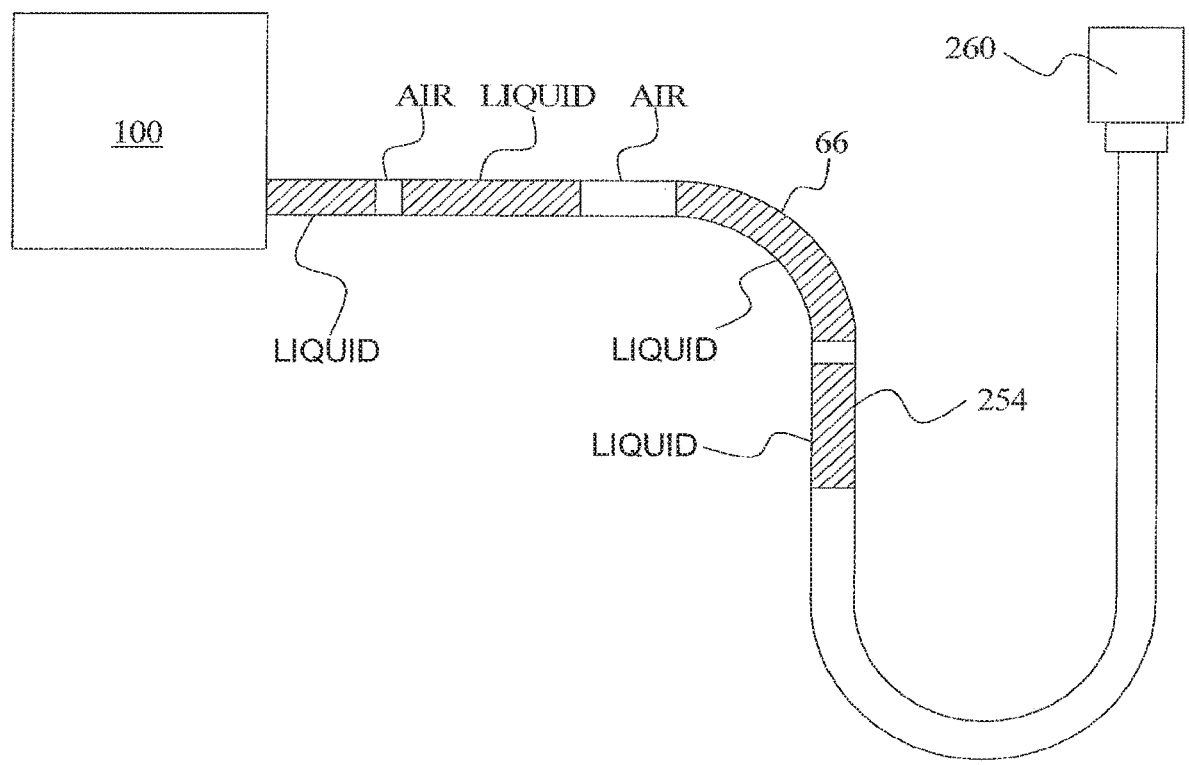

FIG. 22 illustrates another advantage of the priming method of the present invention. A mixture of air and fluid can sometimes appear in the proximal part of the patient line 66, near cassette 100, at the beginning of prime. The mixture is usually near the cassette 100 because fluid may have entered into the line due to procedural errors during the setup procedure. For example, the patient may improperly connect the solution bags and open the clamps when the set is loaded. The mixture of air and fluid 254 can sometimes slow and sometimes prevent proper priming. The pressurized assist beginning in FIG. 18 and ending in FIG. 19 of patient line 66 will typically dislodge or overcome the problems caused by the air/fluid mixture, enabling proper priming.

FIG. 16 discussed above shows one alternative embodiment of the priming method of present invention, wherein system 200 replaces pneumatic pumps P1 and P2 in FIGS. 17 through 21. The pneumatic source of positive pressure used in FIG. 19 is replaced by a mechanical actuator 202, which pushes on a flexible membrane film 203, which in turn is attached to a cassette 210 having sheeting 204 on one side of thereof. System 200 uses a vacuum to force membrane 203 to follow a piston head 206 when head 206 retracts and moves toward cassette 210, drawing fluid into pumping chamber 208 when fluid valve 212 is open. Actuator 202 and head 206 are moved forward when another fluid valve (not shown) is opened, pushing fluid down the patient line. A pressure sensor 214 detects a pressure rise if the patient line is clamped. The position of actuator 202 and head 206 can be used to determine when to open valve 212 so that gravity can complete the priming of the patient line.

Appendix D shows data from the priming method of the present invention. Additionally, the data in Appendix E, Tables 3 and 4, was obtained from a software program that opened valves 256 and 258 when the pressure in pump chambers P1 and P2 fell below 0.2 psig. If the pressure did not fall to below 0.2 psig, the pressure was recorded and a message was logged that stated, "Timeout before PosP reached 0.20 psig". A number of normal primes were performed as well as a number of primes wherein the patient line was clamped near the patient connector at the distal end of the line.

Solution Bag Head Height Determination

Dialysis, such as peritoneal dialysis or hemodialysis or other renal therapies such as hemofiltration or hemodiafiltration can performed using multiple solution bags, such as dialysate bags, lactate bags and/or dextrose bags. In such a case, it is advantageous to determine that the required solution bags are: (i) present and (ii) located at a vertical height suitable to enable the particular therapy to be performed, for example, an automated peritoneal dialysis performed by a machine. Such determinations should be made at the beginning of therapy, e.g., during the priming and cassette integrity tests, so that the machine can alert the patient of any problems before treatment begins and/or before the patient falls asleep.

Figure 23:
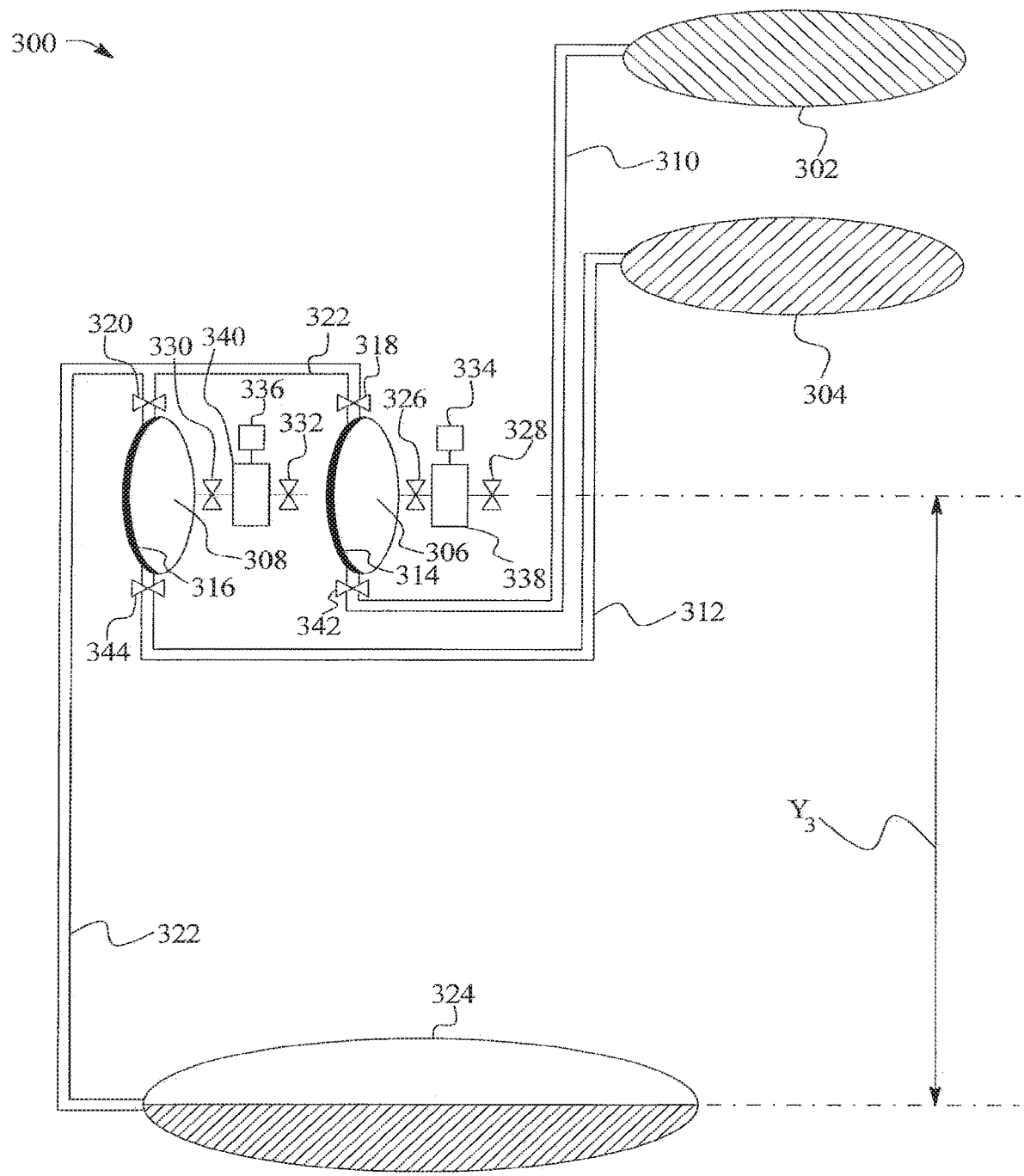
FIGS. 23 and 24 are schematic views illustrating a method and apparatus of the present invention that evaluates solution and drain bag head heights.
Figure 24:
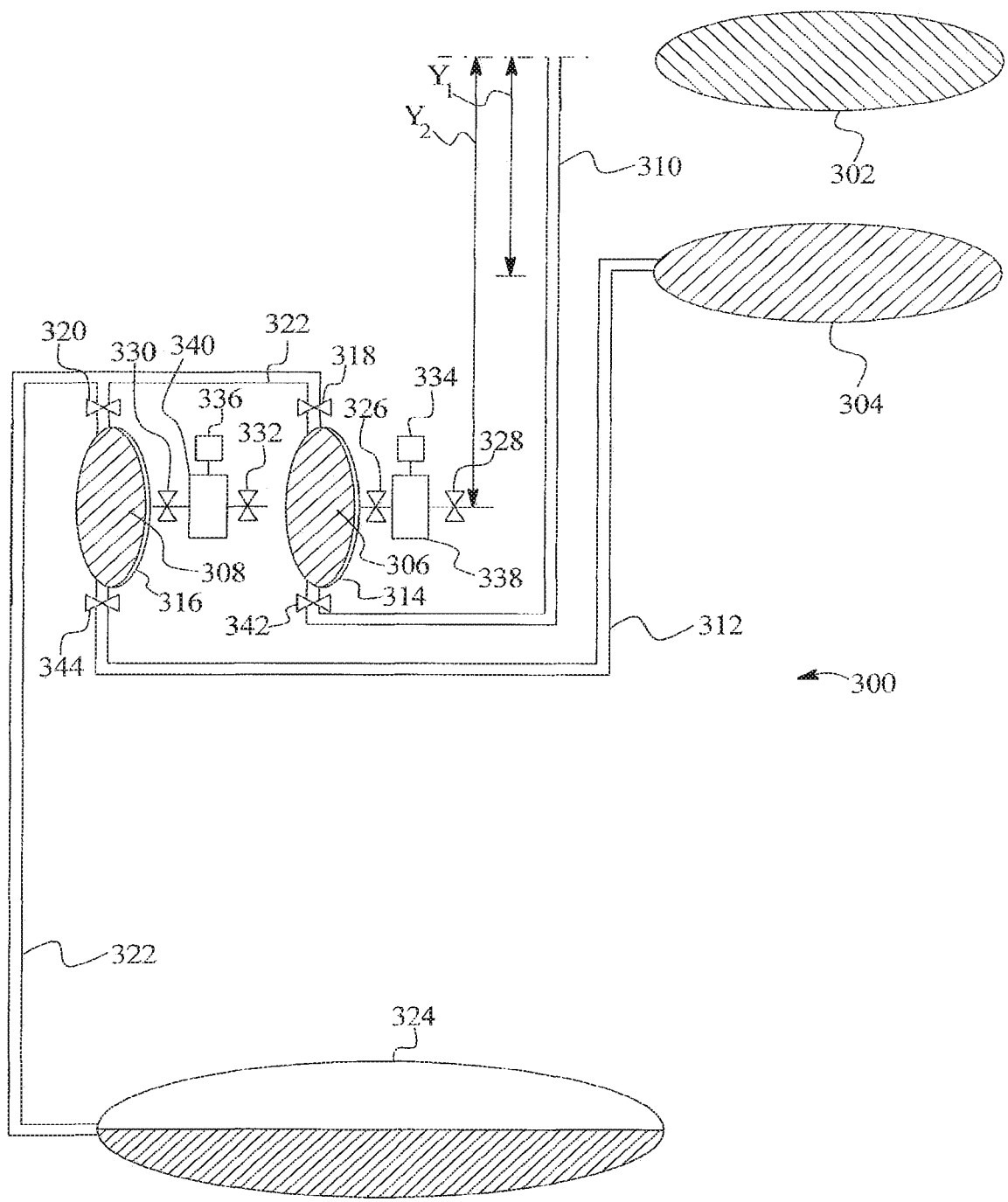

Referring now to FIGS. 23 and 24, a system 300 illustrating one embodiment for determining solution bag head height is illustrated. System 300 of FIG. 23 includes solution bags 302 and 304, which are connected fluidly to pump chambers 306 and 308 via fluid lines 310 and 312, respectively. Pump chambers 306 and 308 house flexible diaphragms 314 and 316, respectively. Dialysate or therapy fluid can flow from pump chambers 306 and 308 when fluid valves 318 and 320 are opened, through fluid pathway 322, to drain bag 324.

System 300 includes valves 326 and 328 connected fluidly to chamber 306 and valves 330 and 332 connected fluidly to chamber 308. Air/vacuum chambers 338 and 340 are placed between valves 326 and 328 and 330 and 332, respectively. Differential pressure sensors 334 and 336 sense differential pressure within chambers 338 and 340, respectively. It should be appreciated that if valves 326, 328, 330 and 332 are open, while pump chambers 306 and 308 are empty, differential pressure sensor 334 (placed between valves 326 and 328) and differential pressure sensor 336 (placed between valves 330 and 332) and are zeroed because the pressures in air/vacuum chambers 338 and 340 are equal to atmospheric pressure.

As seen in FIG. 24, when valves 318, 320, 328 and 332 are closed and fluid valves 326, 330, 342 and 344 are opened, fluid from solution bags 302 and 304 flows vertically down fluid pathways 310 and 312, respectively, into pump chambers 306 and 308. Respective flexible diaphragms 314 and 316 move when fluid flows into pump chambers 306 and 308, causing a pressure rise in the air trapped in air/vacuum chambers 338 and 340. Fluid flows into chambers 306 and 308, through open valves 342 and 344, until the pressure in respective air/vacuum chambers 338 and 340, as measured by pressure sensors 334 and 336, is equal to the pressure exerted by the solution (approximately water for purposes of density) in columns that are equal in height to vertical distances Y1 and Y2.

If the pressure equivalent to that exerted by columns of solution of heights Y1 and Y2 is within a predetermined operating parameter for the medical fluid therapy system 300 (e.g., an APD system), the therapy is allowed to continue. If not, a suitable alarm is posted informing the patient or operator that one or both solution bags 302 or 304 is positioned outside the operating parameters of system 300.

A pressure difference caused by differences in the vertical positions (pressure head heights) of solution bags 302 and 304 also has to be within set limits for system 300 to operate within specification in one embodiment. An inlet side of a pump subjected to a negative head height results in less fluid being pumped for each stroke of chambers 306 and 308, as compared to strokes made when positive head height pressure is seen on the inlet side of a pump. Therefore when equal volumes of different solutions are being pumped by chambers 306 and 308 and mixed at a desired ratio, e.g., 1:1, it is advantageous for the vertical positions and corresponding pressure head heights of the two solutions to be the same or substantially the same.

The previous description of system 300 in FIGS. 23 and 24 illustrates how sensors 334 and 336 can be zeroed and then used to test solution bag height in the context of a filling sequence, i.e., pump chambers 306 and 308 moving from empty towards full. It should be appreciated that conversely, sensors 334 and 336 can be zeroed and then used to test drain bag height in the context of a drain sequence, i.e., pump chambers 306 and 308 moving full or partially full towards empty.

In the drain test, pump chambers 306 and 308 are first filled with fluid from solution bags 302 and 304, respectively, by opening valves 342 and 344, so that therapy fluid flows through fluid pathways 310 and 312, respectively, and into pump chambers 306 and 308 as shown in FIG. 24. Valves 326, 328, 330 and 332 are then opened, allowing the pressure in air/vacuum chambers 334 and 336 to be zeroed with respect to atmospheric pressure and enabling the differential pressure sensor readings of sensors 334 and 336 to be set or reset to zero.

Valves 342, 344, 328 and 332 are then closed and valves 318, 320, 326 and 330 are opened. Fluid flows then from pump chambers 306 and 308, through fluid pathway 322, to drain bag 324. Diaphragms 314 and 316 within pump chambers 306 and 308 move accordingly, creating vacuums respectively inside air/vacuum chambers 338 and 340. Fluid flow stops when the vacuum in air/vacuum chambers 338 and 340, measured by pressure sensors 334 and 336, respectively, is equal to a column of solution (negative pressure head height) of height Y3 shown in FIG. 23.

The drain test ensures that the drain bag/drain line discharge is located below pump chambers 306 and 308, so that no backflow occurs due to gravity. The drain test also ensures that the drain is not located too far below the pumps and valves, wherein the location causes an adverse effect on the operation of the valves. If the pressure equivalent to a column of solution of height Y3 is within a predetermined operating parameter for the medical fluid therapy system 300, the therapy is allowed to continue. If not, a suitable alarm is posted informing the patient or operator that the drain bag 324 is positioned outside the operating parameters of system 300.

It should be understood that various changes and modifications to the presently preferred embodiments described herein will be apparent to those skilled in the art. Such changes and modifications can be made without departing from the spirit and scope of the present invention and without diminishing its intended advantages. It is intended that such changes and modifications be covered by the appended claims.

The invention is claimed as follows:

1. A dialysis system comprising:
a housing;
a pump actuator housed by the housing;
a fluid pumping cassette coupled operably to the housing and including a flexible membrane covering a pump chamber;
a mechanically actuated piston head provided by the pump actuator and positioned to extend towards and away from the fluid pumping cassette, the fluid pumping cassette positioned such that the flexible membrane of the fluid pumping cassette faces the piston head so that the piston head can push the flexible membrane into the pump chamber of the fluid pumping cassette to expel a fluid from the pump chamber; and
a controller programmed to perform a leak test by monitoring a sensed position of the mechanically actuated piston head while the mechanically actuated piston head applies a force to the flexible membrane of the fluid pumping cassette.

2. The dialysis system of claim 1, wherein the membrane is moved by the mechanically actuated piston head during the leak test if a leak is present.

3. The dialysis system of claim 1, wherein the controller is programmed to cause the mechanically actuated piston head to apply a constant force to the flexible membrane of the fluid pumping cassette during the leak test.

4. The dialysis system of claim 1, which includes a vacuum chamber configured to pull a vacuum on the flexible membrane to open the membrane within the pump chamber to fill the pump chamber with the fluid.

5. The dialysis system of claim 1, wherein the sensed position of the mechanically actuated piston head is sensed by a sensor that outputs to the controller.

6. The dialysis system of claim 1, which includes a vacuum chamber configured to pull a vacuum on the flexible membrane to cause the flexible membrane to follow a movement of the mechanically actuated piston head.

7. The dialysis system of claim 6, wherein at least one of the pump actuator or the mechanically actuated piston head is located within the vacuum chamber.

8. The dialysis system of claim 6, which includes a valve actuator housed by the housing, and wherein the fluid pumping cassette includes a valve portion in fluid communication with the pump chamber, the valve portion operable with the valve actuator.

9. The dialysis system of claim 8, wherein the controller is programmed to cause the valve actuator to close the valve portion of the fluid pumping cassette before the leak test begins.

10. The dialysis system of claim 1, wherein the controller is programmed to trigger an alarm if the sensed position of the mechanically actuated piston head moves outside of an allowable range during the leak test.

* * * * *